(12) United States Patent
Okumura

(10) Patent No.: US 10,391,086 B2
(45) Date of Patent: Aug. 27, 2019

(54) USE OF EP4 RECEPTOR ANTAGONISTS IN THE TREATMENT OF CARTILAGE DISEASE

(71) Applicant: AskAt Inc., Aichi (JP)

(72) Inventor: Takako Okumura, Aichi (JP)

(73) Assignee: AskAt Inc., Aichi (JP)

( * ) Notice: Subject to any disclaimer, the term of this patent is extended or adjusted under 35 U.S.C. 154(b) by 0 days.

(21) Appl. No.: 15/911,567

(22) Filed: Mar. 5, 2018

(65) Prior Publication Data

US 2018/0193324 A1    Jul. 12, 2018

Related U.S. Application Data

(63) Continuation-in-part of application No. 14/777,610, filed as application No. PCT/JP2014/001597 on Mar. 19, 2014, now abandoned.

(30) Foreign Application Priority Data

Mar. 19, 2013  (JP) ................................. 2013-057180

(51) Int. Cl.
| | |
|---|---|
| *A61K 31/4439* | (2006.01) |
| *A61K 31/44* | (2006.01) |
| *A61K 45/06* | (2006.01) |
| *A61P 19/02* | (2006.01) |
| *A61K 31/437* | (2006.01) |
| *A61K 31/381* | (2006.01) |

(52) U.S. Cl.
CPC ........ *A61K 31/4439* (2013.01); *A61K 31/381* (2013.01); *A61K 31/437* (2013.01); *A61K 31/44* (2013.01); *A61K 45/06* (2013.01); *A61P 19/02* (2018.01)

(58) Field of Classification Search
None
See application file for complete search history.

(56) References Cited

U.S. PATENT DOCUMENTS 5,843,959 A    12/1998 Bergeron et al.

FOREIGN PATENT DOCUMENTS

| WO | 02/32422 | 4/2002 |
|---|---|---|
| WO | 02/32900 | 4/2002 |
| WO | 2004/067524 | 8/2004 |
| WO | 2005/021508 | 3/2005 |
| WO | 2005/102389 | 11/2005 |
| WO | 2005/105732 | 11/2005 |
| WO | 2006/095268 | 9/2006 |
| WO | 2008/017164 | 2/2008 |
| WO | 2011/124524 | 10/2011 |

OTHER PUBLICATIONS

International Search Report dated Jun. 24, 2014 in International (PCT) Application No. PCT/JP2014/001597.
Attur et al., "Prostaglandin E₂ Exerts Catabolic Effects in Osteoarthritis Cartilage: Evidence for Signaling via the EP4 Receptor", J. Immunol., vol. 181, No. 7, 2008, pp. 5082-5088.
Li et al., "Prostaglandin E₂ and Its Cognate EP Receptors Control Human Adult Articular Cartilage Homeostasis and Are Linked to the Pathophysiology of Osteoarthritis", Arthritis & Rheumatism, vol. 60, No. 2, Feb. 2009, pp. 513-523.
Blouin et al., "The Discovery of 4-{1-[({2,5-Dimethyl-4-[4-{trifluoromethyl)benzyl]-3-thienyl}carbonyl)amino]cyclopropyl}benzoic Acid (MK-2894), A Potent and Selective Prostaglandin E₂ Subtype 4 Receptor Antagonist", J. Med. Chem., vol. 53, 2010, pp. 2227-2238.
Extended European Search Report dated Oct. 25, 2016 in corresponding European Application No. 14768803.0.
Murase et al., "Effect of prostanoid EP₄ receptor antagonist, CJ-042,794, in rat models of pain and inflammation", European Journal of Pharmacology, vol. 580, No. 1-2, Feb. 1, 2008, pp. 116-121, XP055077159.
Okumura et al., "Effects of the selective EP4 antagonist, CJ-023,423 on chronic inflammation and bone destruction in rat adjuvant-induced arthritis", Journal of Pharmacy and Pharmacology, vol. 60, No. 6, Jun. 1, 2008, pp. 723-730, XP002712071.
Naik et al., "Arthritis, a complex connective and synovial joint destructive autoimmune disease: Animal models of arthritis with varied etiopathology and their significance", Journal of Postgraduate Medicine, vol. 60, Issue 3, pp. 309-317 (Jul. 2014).
Communication pursuant to Article 94(3) EPC issued May 23, 2019 in corresponding European Patent Application No. 14768803.0.

*Primary Examiner* — Sreenivasan Padmanabhan
*Assistant Examiner* — Jody L Karol
(74) *Attorney, Agent, or Firm* — Wenderoth, Lind & Ponack, L.L.P.

(57) ABSTRACT

The invention is a method of treating osteoarthritis or normalizing a condition of osteoarthritis comprising administering to an animal or a human in need thereof a therapeutically effective amount of 3-[2-(4-{2-ethyl-4,6-dimethyl-1H-imidazo[4,5-c]pyridin-1-yl}phenyl)ethyl]-1-[(4-methylbenzene)sulfonyl]urea or a pharmaceutically acceptable salt thereof.

8 Claims, 1 Drawing Sheet

{Fig. 1}
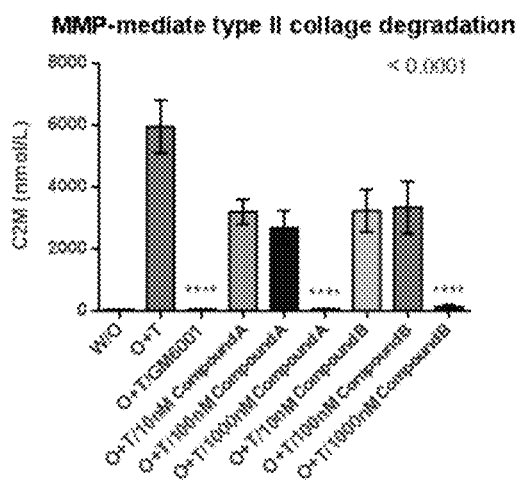
{Fig. 2}
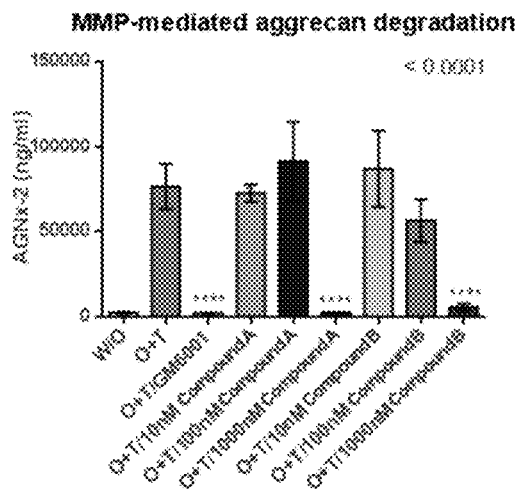

USE OF EP4 RECEPTOR ANTAGONISTS IN THE TREATMENT OF CARTILAGE DISEASE

TECHNICAL FIELD

This invention relates to compounds for use in therapeutic treatment of the human body. In particular, it relates to compounds with selective EP4 receptor antagonism which are useful for treating cartilage disease, or preventing or delaying the onset or the progression of the said disease.

This invention also relates to a pharmaceutical composition for the treatment of cartilage disease which comprises a therapeutically effective amount of a compound of formula (I), (II), (III), (IV), (Va) or (Vb), or a pharmaceutically acceptable salt thereof. This invention relates to a method for the treatment of cartilage disease in an animal subject including a mammalian subject, which comprises administering to the animal subject including a mammalian subject a compound of the formula (I), (II), (III), (IV), (Va) or (Vb), or a pharmaceutically acceptable salt thereof. Further this invention relates to a method for the treatment of cartilage disease in an animal subject including a mammalian subject, which comprises administering to the animal subject including a mammalian subject in need a therapeutically effective amount of a compound of the formula (I), (II), (III), (IV), (Va) or (Vb), or a pharmaceutically acceptable salt thereof.

BACKGROUND ART

An articular disorder is a disease whose major lesion is a degeneration of an articular cartilage. Cartilage is the organization composed by collagen and proteoglycan. Due to various causes, the synthesizing ability of proteoglycan in this cartilage organization declines, and proteoglycan starts to be released from the organization. The release of type-I collagenase (metalloprotease I) is simultaneously increased, and collagen of the cartilage organization is resolved. The destruction of the cartilage organization proceeds due to a series of these responses. And it undergoes, depending on the stage of the lesion, a hyperplasia of a synovial membrane, a destruction of a subcartilaginous bone, a hyperplasia or a neoplasia of a circumarticular cartilage, which are followed by a deformation of the cartilage, which may lead to dysfunction in a serious case. While the articular disorder occurs most frequently in a knee joint, it occurs also in the joints of elbows, thighs, legs and fingers. Among the articular diseases, the disease which is observed in the largest number of patients is an osteoarthritis, and it is considered to occur increasingly in an elderlies-dominating society in near future, since one of its causes is considered to be the aging of a human. For treating this, an analgesic antiinflammatory agent or a hyaluronic acid formulation is employed to remedy the pain due to cartilage degeneration or subcartilaginous bone destruction. However, all therapeutic methods are only nosotropic, and exhibit no sufficient effects. Suppression of cartilage destruction, promotion of chondrogenesis and induction of cartilage cell differentiation are considered to be effective in prevention and treatment of a cartilage disease.

In the field of therapeutic and prophylactic agents against cartilage diseases which are no more than nosotropic currently, a novel cartilage disease preventing and/or treating agent which is rather radical and excellent in terms of the characteristics required in a useful pharmaceutical (e.g., such as stability, absorption, bioavailability) is demanded.

Prostaglandin E2 (PGE2) is a potent modulator involved in the pathogenesis of a variety of diseases such as inflammation, pain, arthritis, and cancer. PGE2 binds to at least four subtypes of PGE receptor, designated EP1, EP2, EP3, and EP4. Molecular pharmacology studies have revealed that all subtypes are 7-transmembrane spanning receptors that belong to the G-protein coupled receptor superfamily. EP1 activation stimulates the release of intracellular calcium; EP2 and EP4 stimulation both activate adenylate cyclase but differ in their response to certain ligands; and EP3 stimulation inhibits adenylate cyclase via inhibitory G-proteins (NPL 1).

Many compounds which show EP4 receptor antagonism have been reported. However it has never been reported that compounds with selective EP4 receptor antagonism which are useful for treating cartilage disease.

CITATION LIST

Non Patent Literature

{NPL 1}
Biochim Biophys Acta 1259: 109-19, 1995

SUMMARY OF INVENTION

Technical Problem

As mentioned above, for treating cartilage disease, all therapeutic methods are only nosotropic, and exhibit no sufficient effects. Therefore the compounds which are truly effective for cartilage disease are strongly desired.

In particular, an object of the present invention is to provide compounds with selective EP4 receptor antagonism which are useful for treating cartilage disease, or preventing or delaying the onset or the progression of cartilage disease.

An object of the present invention is to provide a pharmaceutical composition for the treatment of cartilage disease which comprises a therapeutically effective amount of a compound of formula (I), (II), (III), (IV), (Va) or (Vb), or a pharmaceutically acceptable salt thereof. An object of the present invention is to provide a method for the treatment of cartilage disease in an animal subject including a mammalian subject, which comprises administering to the animal subject including a mammalian subject a compound of the formula (I), (II), (III), (IV), (Va) or (Vb), or a pharmaceutically acceptable salt thereof. Further an object of the present invention is to provide a method for the treatment of cartilage disease in an animal subject including a mammalian subject, which comprises administering to the animal subject including a mammalian subject in need a therapeutically effective amount of a compound of the formula (I), (II), (III), (IV), (Va) or (Vb), or a pharmaceutically acceptable salt thereof.

Solution to Problem

The present inventors made much effort to develop a pharmaceutical capable of exerting a direct effect on a cartilage cell to suppress a cartilage destruction and also capable of promoting cartilaginous osteoanagenesis, and finally discovered that a compound of formula (I), (II), (III), (IV), (Va) or (Vb), or a pharmaceutically acceptable salt thereof guarantees beneficial effects on cytokine-induced cartilage calcification in a full-depth articular explants model, rat mono-iodoacetate and/or meniscal transection model, rat meniscal transection and/or ovariectomised model, which clearly are useful for prevention and/or treatment of a cartilage disease.

Specifically, the gist of the present invention is as follows:

[1] Use of a compound with EP4 antagonistic activity, or a pharmaceutically acceptable salt thereof in the manufacture of a medicament for the treatment of cartilage diseases in an animal subject including a mammalian subject;

[2] Use of a compound of the formula (I), (II), (III), (IV), (Va) or (Vb), or a pharmaceutically acceptable salt thereof in the manufacture of a medicament for the treatment of cartilage diseases in an animal subject including a mammalian subject:

{Chem. 1}

(I)

wherein $Y^1$, $Y^2$, $Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$ alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$ alkyl-C(O)—N($R^3$)—, $Q^1$-$C_{1-4}$ alkyl-N($R^3$)— or $C_{1-4}$ alkyl-C(O)—N($R^3$)—;

$Q^1$ is a 5 to 12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or NH$_2$(HN=)C—;

A is a 5 or 6 membered monocyclic aromatic ring optionally containing up to 3 heteroatoms selected from O, N and S, wherein said 5 or 6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, acetyl, $R^3$N($R^4$)C(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)— and NH$_2$(HN=)C—; B is halo-substituted $C_{1-6}$ alkylene, $C_{3-7}$ cycloalkylene, $C_{2-6}$ alkenylene, $C_{2-6}$ alkynylene, —O—$C_{1-5}$ alkylene, $C_{1-2}$ alkylene-O—$C_{1-2}$ alkylene or $C_{1-6}$ alkylene optionally substituted with an oxo group or $C_{1-3}$ alkyl;

W is NH, N—$C_{1-4}$ alkyl, O, S, N—$OR^5$ or a covalent bond;

$R^2$ is H, $C_{1-4}$ alkyl, OH or $C_{1-4}$ alkoxy;

Z is a 5 to 12 membered monocyclic or bicyclic aromatic ring optionally containing up to 3 heteroatoms selected from O, N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, $R^3$C(=O)N($R^4$)—, HO(O=)C—, $C_{1-4}$ alkyl-O(O=)C—, $C_{1-4}$ alkylsulfonylamino, $C_{3-7}$ cycloalkyl, NH$_2$(HN=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, $C_{1-4}$ alkylthio, nitro, amino, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, NH$_2$(HN=)C—, $R^3$N($R^4$)C(=O)—, $R^3$N($R^4$)S(O)m-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl;

$R^5$ is H, $C_{1-4}$ alkyl, $C_{1-4}$ alkyl-(O=)C— or $C_{1-4}$ alkyl-O—(O=)—C—; and $Q^2$ is a 5 to 12 membered monocyclic or bicyclic aromatic ring, optionally containing up to 3 heteroatoms selected from O, N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl) amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3$($R^4$)C(=O)N—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O)NH— or NH$_2$(HN=)C—;

{Chem. 2}

(II)

wherein A represents a phenyl group or a pyridyl group;

B represents an aryl group or a heteroaryl group;

E represents a 1,4-phenylene group;

$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

$R^3$ and $R^4$ independently represent a hydrogen atom or an alkyl group having from 1 to 4 carbon atoms; or $R^3$ and $R^4$ may be joined together to form an alkylene chain having 2 to 6 carbon atoms;

$R^5$ represents —$CO_2H$, $CO_2W$,

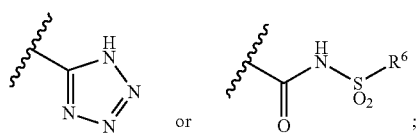

{Chem. 3}

$R^6$ represents an alkyl group having from 1 to 6 carbon atoms, a cycloalkyl group having from 3 to 7 ring atoms, an aryl group or a heteroaryl group;

X represents a methylene group, an oxygen atom or a sulfur atom;

said aryl groups have from 6 to 10 carbon atoms;

said heteroaryl groups are 5 to 10-membered aromatic heterocyclic groups containing from 1 to 3 heteroatoms selected from the group consisting of sulfur atom, oxygen atom and nitrogen atom;

said aryl groups and said heteroaryl groups referred to in the definitions of B are unsubstituted or are substituted by at least one substituent selected from the group consisting of substituents alpha;

said 1,4-phenylene group referred to in the definition of E is unsubstituted or is substituted by at least one substituent selected from the group consisting of substituents beta;

said aryl groups and said heteroaryl groups referred to in the definitions of $R^6$ and alpha are unsubstituted or are substituted by at least one substituent selected from the group consisting of substituents beta;

said substituents alpha are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent alpha groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl (alkyl) amino groups having from 1 to 6 carbon atoms, alkanoylaminoalkyl groups having from 1 to 6 carbon atoms in both the alkanoyl and alkyl part, alkanoyl (alkyl) aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

said substituents beta are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

W is a pharmaceutically acceptable ester prodrug group; with the proviso $R^1$ and $R^2$ do not represent a hydrogen atom simultaneously;

{Chem. 4}

(III)

wherein X represents —CH— or a nitrogen atom;

Y represents —$NR^4$, an oxygen atom or a sulfur atom;

$R^4$ represents a hydrogen atom or an alkyl group having from 1 to 3 carbon atoms;

Z represents a hydrogen atom or a halogen atom;

$R^1$ represents an alkyl group having from 1 to 6 carbon atoms optionally substituted with an alkoxy group having from 1 to 6 carbon atoms or a cycloalkyl group having from 3 to 7 carbon atoms; a cycloalkyl group having from 3 to 7 carbon atoms optionally substituted with an alkyl group having from 1 to 3 carbon atoms; a phenyl group optionally substituted with one or more substituents alpha; or a group $Het^1$ optionally substituted with one or more substituents alpha;

$Het^1$ represents a heterocyclic group having from 4 to 7 ring atoms which contains either from 1 to 4 nitrogen ring heteroatoms or from 0 to 2 nitrogen ring heteroatoms and 1 oxygen or 1 sulfur ring heteroatom;

$R^2$ and $R^3$ independently represent a hydrogen atom or an alkyl group having from 1 to 3 carbon atoms; or $R^2$ and $R^3$ together form an alkylene chain having from 3 to 6 carbon atoms; and said substituent alpha is selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms, alkanoyl groups having from 2 to 5 carbon atoms, alkenyl groups having from 2 to 4 carbon atoms, alkynyl groups having from 2 to 4 carbon atoms, alkylthio groups having from 1 to 4 carbon atoms, nitro groups, amino groups, mono- or di-alkylamino groups having from 1 to 4 carbon atoms, aminosulfonyl groups, alkoxycarbonyl groups having from 1 to 4 carbon atoms, alkylsulfonylamino groups having from 1 to 4 carbon atoms, cycloalkyl groups having from 3 to 7 carbon atoms and a mono- or di-alkylaminocarbonyl groups having from 1 to 6 carbon atoms;

or a pharmaceutically acceptable ester of such compound;

{Chem. 5}

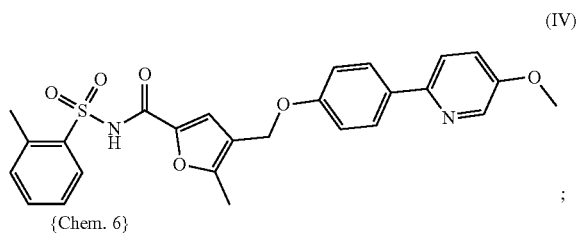

(IV)

{Chem. 6}

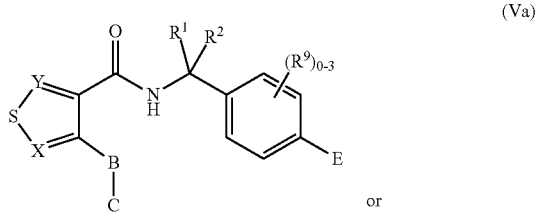

(Va)

or

{Chem. 7}

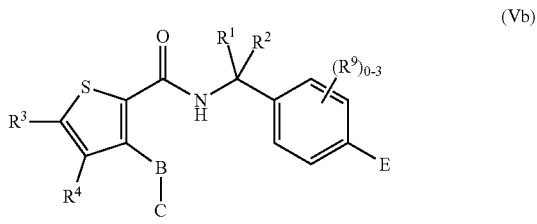

(Vb)

wherein X and Y are independently selected from the group consisting of: N and C($R^{11}$), wherein each $R^{11}$ is independently selected from the group consisting of: hydrogen, halo and $C_{1-4}$alkyl;

B is selected from the group consisting of: —C($R^5$)($R^6$)—, —O—, —S—, —S(O)—, —SO$_2$—, —C($R^5$)($R^6$)—C($R^7$)($R^8$)—, —O—C($R^5$)($R^6$)—, —S—C($R^5$)($R^6$)—, —S(O)—C($R^5$)($R^6$)— and —SO$_2$—C($R^5$)($R^6$)—;

C is selected from the group consisting of aryl and heteroaryl, or a fused analog of aryl or heteroaryl, each optionally substituted with one to three substituents independently selected from $R^{10}$;

E is selected from the group consisting of: —C(O)OH, —C(O)OC$_{1-4}$alkyl, tetrazolyl and {Chem. 8}

wherein R is selected from the group consisting of: $C_{1-4}$alkyl, aryl and heteroaryl, or a fused analog of aryl or heteroaryl, wherein aryl and heteroaryl or the fused analogs thereof are optionally substituted with one to three substituents independently selected from $R^{10}$;

$R^1$ to $R^8$ are independently selected from the group consisting of: H, halo, —O—$R^{12}$, $C_{1-6}$alkyl and $C_{3-6}$cycloalkyl, and one or more pairs of $R^1$ and $R^2$, $R^5$ and $R^6$, and $R^7$ and $R^8$ may be joined together with the carbon atom to which they are attached to form a 3- to 5-membered monocyclic cycloalkyl ring, and $R^5$ and $R^6$ or $R^7$ and $R^8$ may be joined together to form carbonyl;

$R^9$ is independently selected from the group consisting of: halo, hydroxyl and $C_{1-4}$alkyl;

$R^{10}$ is selected from the group consisting of: halo, cyano, $C_{1-4}$alkyl, $C_{1-4}$fluoroalkyl, $C_{1-4}$alkoxy, $C_{1-4}$thioalkoxy and $C_{1-4}$fluoroalkoxy; and each $R^{12}$ is selected from the group consisting of: H, $C_{1-4}$alkyl, $C_{3-6}$cycloalkyl and heterocyclyl;

[3] The use of [2], wherein the compound of (I), (II), (III), (IV), (Va) or (Vb) is selected from:

3-[2-(4-{2-ethyl-5,7-dimethyl-3H-imidazo[4,5-b]pyridin-3-yl}phenyl)ethyl]-1-[(4-methylbenzene)sulfonyl]urea;

3-[2-(4-{2-ethyl-4,6-dimethyl-1H-imidazo[4,5-c]pyridin-1-yl}phenyl)ethyl]-1-[(4-methylbenzene)sulfonyl]urea;

1-{2-[4-(5-acetyl-2-ethyl-1H-1,3-benzodiazol-1-yl)phenyl]ethyl}-3-[(4-methylbenzene)sulfonyl]urea;

3-{2-[4-(2-ethyl-5-methoxy-1H-1,3-benzodiazol-1-yl)phenyl]ethyl}-1-[(4-methylbenzene)sulfonyl]urea;

2-{4-[6-chloro-2-ethyl-5-(trifluoromethyl)-1H-1,3-benzodiazol-1-yl]phenyl}ethyl N-[(4-methylbenzene)sulfonyl]carbamate;

3-{2-[4-(6-chloro-5-cyano-2-ethyl-1H-1,3-benzodiazol-1-yl)phenyl]ethyl}-1-[(4-methylbenzene)sulfonyl]urea;

2-(4-{2-ethyl-4,6-dimethyl-1H-imidazo[4,5-c]pyridin-1-yl}phenyl)ethyl N-[(4-methylbenzene)sulfonyl]carbamate;

2-(4-{2-tert-butyl-4,6-dimethyl-1H-imidazo[4,5-c]pyridin-1-yl}phenyl)ethyl N-[(4-methylbenzene)sulfonyl]carbamate;

2-[4-(5-carbamoyl-6-chloro-2-ethyl-1H-1,3-benzodiazol-1-yl)phenyl]ethyl N-[(4-methylbenzene)sulfonyl]carbamate;

1-(2-{4-[2-ethyl-5-(1-hydroxyethyl)-1H-1,3-benzodiazol-1-yl]phenyl}ethyl)-3-[(4-methylbenzene)sulfonyl]urea;

1-(2-{4-[6-chloro-2-(2-hydroxypropan-2-yl)-5-(trifluoromethyl)-1H-1,3-benzodiazol-1-yl]phenyl}ethyl)-3-[(4-methylbenzene)sulfonyl]urea;

2-{4-[6-chloro-2-(pyridin-2-yl)-5-(trifluoromethyl)-1H-1,3-benzodiazol-1-yl]phenyl}ethyl N-[(4-methylbenzene)sulfonyl]carbamate;

3-(2-{5-[6-chloro-2-ethyl-5-(trifluoromethyl)-1H-1,3-benzodiazol-1-yl]pyridin-2-yl}ethyl)-1-[(4-methylbenzene)sulfonyl]urea;

2-{4-[6-chloro-2-ethyl-5-(trifluoromethyl)-1H-1,3-benzodiazol-1-yl]phenyl}ethyl N-[(2-chlorobenzene)sulfonyl]carbamate;

3-(2-{4-[5,7-dimethyl-2-(methylamino)-3H-imidazo[4,5-b]pyridin-3-yl]phenyl}ethyl)-1-[(4-methylbenzene)sulfonyl]urea;

4-((1S)-1-{[5-chloro-2-(4-fluorophenoxy)benzoyl]amino}ethyl)benzoic acid;

4-[(1S)-1-({[5-chloro-2-(4-fluorophenoxy)pyridin-3-yl]carbonyl}amino)ethyl]benzoic acid;

4-[(1S)-1-({[5-chloro-2-(3-cyanophenoxy)pyridin-3-yl]carbonyl}amino)ethyl]benzoic acid;

4-[(1S)-1-({[5-chloro-2-(3-fluorophenoxy)pyridin-3-yl]carbonyl}amino)ethyl]benzoic acid;

4-[(1S)-1-({[5-chloro-2-(3-chlorophenoxy)pyridin-3-yl]carbonyl}amino)ethyl]benzoic acid;

4-((1S)-1-{[5-chloro-2-(3-fluorophenoxy)benzoyl]
   amino}ethyl)benzoic acid;
4-((1S)-1-{[5-chloro-2-(3-chlorophenoxy)benzoyl]
   amino}ethyl)benzoic acid;
4-[(1S)-1-({[5-chloro-2-(2-chloro-4-fluorophenoxy)pyri-
   din-3-yl]carbonyl}amino)ethyl]benzoic acid;
4-[(1S)-1-({[5-chloro-2-(3,4-difluorophenoxy)pyridin-3-yl]
   carbonyl}amino)ethyl]benzoic acid;
4-[(1S)-1-({[5-chloro-2-(2,3-difluorophenoxy)pyridin-3-yl]
   carbonyl}amino)ethyl]benzoic acid;
4-((1S)-1-{[5-chloro-2-(2,3-difluorophenoxy)benzoyl]
   amino}ethyl)benzoic acid;
4-((1S)-1-{[5-chloro-2-(3,4-difluorophenoxy)benzoyl]
   amino}ethyl)benzoic acid;
4-[(1S)-1-({[5-chloro-2-(3-chloro-5-fluorophenoxy)pyri-
   din-3-yl]carbonyl}amino)ethyl]benzoic acid;
4-[(1S)-1-({5-chloro-2-[(4-chlorophenoxy)methyl]
   benzoyl}amino)ethyl]benzoic acid;
4-[(1S)-1-({5-chloro-2-[(3-chlorophenoxy)methyl]
   benzoyl}amino)ethyl]benzoic acid;
4-[(1S)-1-({5-chloro-2-[(4-fluorophenoxy)methyl]
   benzoyl}amino)ethyl]benzoic acid;
4-[(1S)-1-({5-chloro-2-[(3,4-difluorophenoxy)methyl]
   benzoyl}amino)ethyl]benzoic acid;
4-[(1S)-1-({5-chloro-2-[(2,4-difluorophenoxy)methyl]
   benzoyl}amino)ethyl]benzoic acid;
4-{(1S)-1-[({5-chloro-2-[(3-chlorophenoxy)methyl]pyri-
   din-3-yl}carbonyl)amino]ethyl}benzoic acid;
4-[(1S)-1-({5-chloro-2-[(3,5-difluorophenoxy)methyl]
   benzoyl}amino)ethyl]benzoic acid;
4-[(1S)-1-({5-chloro-2-[(3-fluorophenoxy)methyl]
   benzoyl}amino)ethyl]benzoic acid;
4-{(1S)-1-[({2-[(4-chlorophenoxy)methyl]-5-fluoropyridin-
   3-yl}carbonyl)amino]ethyl}benzoic acid;
4-{(1S)-1-({5-chloro-2-[(cyclohexylmethoxy)methyl]
   benzoyl}amino)ethyl}benzoic acid;
4-((4-(5-methoxypyridin-2-yl)phenoxy)methyl)-5-methyl-
   N-(o-tolylsulfonyl)furan-2-carboxamide,
5-chloro-3-[(3-chlorophenyl)methyl]-N-[1-[4-(2H-tetrazol-
   5-yl)phenyl]ethyl]-2-thiophenecarboxamide,
2,5-dimethyl-N-[(1S)-1-[4-[[(methylsulfonyl)amino]carbo-
   nyl]phenyl]ethyl]-4-[[4-(trifluoromethyl)phenyl]methyl]-
   3-thiophenecarboxamide,
2,5-dimethyl-N-[(1S)-1-[4-[[(phenylsulfonyl)amino]carbo-
   nyl]phenyl]ethyl]-4-[[4-(trifluoromethyl)phenyl]methyl]-
   3-thiophenecarboxamide,
2,5-dimethyl-N-[1-[4-(2H-tetrazol-5-yl)phenyl]cyclopro-
   pyl]-4-[[3-(trifluoromethyl)phenyl]methyl]-3-thiophen-
   ecarboxamide,
2,5-dimethyl-N-[1-[4-(2H-tetrazol-5-yl)phenyl]cyclopro-
   pyl]-4-[[4-(trifluoromethyl)phenyl]methyl]-3-thiophen-
   ecarboxamide,
2-chloro-4-[[[[4-[(3-chlorophenyl)methyl]-2,5-dimethyl-3-
   thienyl]carbonyl]amino]methyl]-benzoic acid,
4-[(1R)-1-[[[2,5-dichloro-4-[(3-chlorophenyl)methyl]-3-
   thienyl]carbonyl]amino]ethyl]-benzoic acid,
4-[(1S)-1-[[[2,5-dibromo-4-[(3-chlorophenyl)methyl]-3-
   thienyl]carbonyl]amino]ethyl]-benzoic acid,
4-[(1S)-1-[[[2,5-dichloro-4-(3-chlorobenzoyl)-3-thienyl]
   carbonyl]amino]ethyl]-benzoic acid,
4-[(1S)-1-[[[2,5-dichloro-4-[(3-chlorophenyl)[(tetrahydro-
   2H-pyran-2-yl)oxy]methyl]-3-thienyl]carbonyl]amino]
   ethyl]-benzoic acid,
4-[(1S)-1-[[[2,5-dichloro-4-[(3-chlorophenyl)hydroxym-
   ethyl]-3-thienyl]carbonyl]amino]ethyl]-benzoic acid,
4-[(1S)-1-[[[2,5-dichloro-4-[(3-chlorophenyl)methyl]-3-
   thienyl]carbonyl]amino]ethyl]-benzoic acid,
4-[(1S)-1-[[[2,5-dichloro-4-[[3-(trifluoromethyl)phenyl]
   methyl]-3-thienyl]carbonyl]amino]ethyl]-benzoic acid,
4-[(1S)-1-[[[2,5-dimethyl-4-[[3-(trifluoromethyl)phenyl]
   methyl]-3-thienyl]carbonyl]amino]ethyl]-benzoic acid,
4-[(1S)-1-[[[2,5-dimethyl-4-[[4-(trifluoromethyl)phenyl]
   methyl]-3-thienyl]carbonyl]amino]ethyl]-benzoic acid,
4-[(1S)-1-[[[2,5-dimethyl-4-[[4-(trifluoromethyl)phenyl]
   methyl]-3-thienyl]carbonyl]amino]ethyl]-benzoic acid,
4-[(1S)-1-[[[4-[(3-chlorophenyl)methyl]-2,5-dimethyl-3-
   thienyl]carbonyl]amino]ethyl]-benzoic acid,
4-[(1S)-1-[[[4-[(3-chlorophenyl)methyl]-3-thienyl]carbo-
   nyl]amino]ethyl]-benzoic acid,
4-[(1S)-1-[[[4-[(4-chlorophenyl)methyl]-2,5-dimethyl-3-
   thienyl]carbonyl]amino]ethyl]-benzoic acid,
4-[(1S)-1-[[[5-bromo-4-[(3-chlorophenyl)methyl]-3-thie-
   nyl]carbonyl]amino]ethyl]-benzoic acid,
4-[[[[2,5-dichloro-4-[(3-chlorophenyl)methyl]-3-thienyl]
   carbonyl]amino]methyl]-benzoic acid,
4-[1-[[[2,5-dimethyl-4-[[3-(trifluoromethyl)phenyl]
   methyl]-3-thienyl]carbonyl]amino]cyclopropyl]-benzoic
   acid,
4-[1-[[[5-chloro-3-[(3-chlorophenyl)methyl]-2-thienyl]car-
   bonyl]amino]ethyl]-benzoic acid, and
4-{1-[({2,5-dimethyl-4-[4-(trifluoromethyl)benzyl]-3-
   thienyl}carbonyl)amino]cyclopropyl}benzoic acid,
or a pharmaceutically acceptable salt thereof;
[4] The use of [2] or [3], wherein the compound of (I), (II),
(III), (IV), (Va) or (Vb) is selected from:
3-[2-(4-{2-ethyl-4,6-dimethyl-1H-imidazo[4,5-c]pyridin-1-
   yl}phenyl)ethyl]-1-[(4-methylbenzene)sulfonyl]urea;
4-[(1S)-1-({[5-chloro-2-(3-fluorophenoxy)pyridin-3-yl]
   carbonyl}amino)ethyl]benzoic acid;
4-{(1S)-1-[({5-chloro-2-[(3-chlorophenoxy)methyl]pyri-
   din-3-yl}carbonyl)amino]ethyl}benzoic acid;
4-((4-(5-methoxypyridin-2-yl)phenoxy)methyl)-5-methyl-
   N-(o-tolylsulfonyl)furan-2-carboxamide;
4-{1-[({2,5-dimethyl-4-[4-(trifluoromethyl)benzyl]-3-
   thienyl}carbonyl)amino]cyclopropyl}benzoic acid,
or a pharmaceutically acceptable salt thereof;
[5] The use of [4], wherein the compound of (I), (II), (III) or
(IV) is selected from:
3-[2-(4-{2-ethyl-4,6-dimethyl-1H-imidazo[4,5-c]pyridin-1-
   yl}phenyl)ethyl]-1-[(4-methylbenzene)sulfonyl]urea;
4-[(1S)-1-({[5-chloro-2-(3-fluorophenoxy)pyridin-3-yl]
   carbonyl}amino)ethyl]benzoic acid;
4-{(1S)-1-[({5-chloro-2-[(3-chlorophenoxy)methyl]pyri-
   din-3-yl}carbonyl)amino]ethyl}benzoic acid; and
4-((4-(5-methoxypyridin-2-yl)phenoxy)methyl)-5-methyl-
   N-(o-tolylsulfonyl)furan-2-carboxamide,
or a pharmaceutically acceptable salt thereof;
[6] The use of any one of [2] to [5], wherein the compound
of the formula (I), (II), (III), (IV), (Va) or (Vb), or the
pharmaceutically acceptable salt is used in combination with
one or more additional compounds known to be useful in the
treatment or prevention of cartilage disease or the symptoms
thereof;
[7] The use of [6], wherein the one or more additional
compounds known to be useful in the treatment or preven-
tion of cartilage disease or the symptoms thereof are selected
from NSAIDs, COX-2 inhibitors, steroids, matrix metallo-
proteinase inhibitors and hyaluronic acid;
[8] A pharmaceutical composition for the treatment of
cartilage disease which comprises a therapeutically effective
amount of a compound of the formula (I), (II), (III), (IV),
(Va) or (Vb) in [2] or a pharmaceutically acceptable salt
thereof;

[9] The pharmaceutical composition of [8], which further comprises a therapeutically effective amount of one or more additional compounds known to be useful in the treatment or prevention of cartilage disease or the symptoms thereof;
[10] A method for the treatment of cartilage disease in an animal subject including a mammalian subject, which comprises administering to the animal subject including a mammalian subject a compound of the formula (I), (II), (III), (IV), (Va) or (Vb) in [2] or a pharmaceutically acceptable salt thereof;
[11] The method of [10], which further comprises administering a therapeutically effective amount of one or more additional compounds known to be useful in the treatment or prevention of cartilage disease thereof;
[12] A method for the treatment of cartilage diseases, which comprises administering to an animal subject including a mammalian subject in need a therapeutically effective amount of a compound of the formula (I), (II), (III), (IV), (Va) or (Vb) in [2] or a pharmaceutically acceptable salt thereof;
[13] The method of [12], which further comprises administering a therapeutically effective amount of one or more additional compounds known to be useful in the treatment or prevention of cartilage disease thereof; and
[14] A compound of the formula (I), (II), (III), (IV), (Va) or (Vb) in [2] or a pharmaceutically acceptable salt thereof for use in the treatment of cartilage diseases in an animal subject including a mammalian subject.

Advantageous Effects of Invention

Namely, the present inventors have discovered that a compound of formula (I), (II), (III), (IV), (Va) or (Vb), or a pharmaceutically acceptable salt thereof shows: 1) dose-dependent inhibition of cartilage destruction in ex vivo bovine cartilage explant model, 2) dose-dependent inhibition of cartilage destruction and serum biochemical markers associated with cartilage degradation in the rat mono-iodo-acetate and/or meniscal transection model, and 3) inhibition of cartilage destruction and serum biochemical markers associated with cartilage degradation in a dose-dependent manner in the rat meniscal transection and/or ovariectomised model.

These results clearly show that a compound of formula (I), (II), (III), (IV), (Va) or (Vb), or a pharmaceutically acceptable salt thereof is useful for the treatment and/or prevention of cartilage disease.

BRIEF DESCRIPTION OF DRAWINGS

In the section "Brief Description of Drawings", the sign "+/−" represents "plus or minus".
FIG. 1 is a graph showing that accumulated release of the C2M to the conditioned medium.
P-value of the ANOVA test is shown in the right-hand corner.
**** $p<0.0001$. Mean+/−SEM. O: oncostatin M, T: TNF-alpha
FIG. 2 is a graph showing that accumulated release of the AGNx2 to the conditioned medium. P-value of the ANOVA test is shown in the right-hand corner.
**** $p<0.0001$. Mean+/−SEM. O: oncostatin M, T: TNF-alpha

DESCRIPTION OF EMBODIMENTS

The present invention features the use of an EP4 receptor antagonist in the manufacture of a medicament for the treatment of cartilage diseases.

In a further aspect the invention features a method of treating cartilage diseases in an animal subject including a mammalian subject, for example, a mammal, including man, comprising administration of an effective amount of an EP4 receptor antagonist.

The term "animal subject," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese.

In a further aspect the invention features a pharmaceutical composition comprising an EP4 receptor antagonist for use in the treatment of cartilage diseases.

Preferably, the EP4 receptor antagonist used in this invention is a selective EP4 receptor antagonist.

In another preferred aspect, the EP4 receptor ligand (antagonist), which is disclosed in WO 02/32900, is an aryl or heteroaryl fused imidazole compound of the following Formula (I)

{Chem. 9}

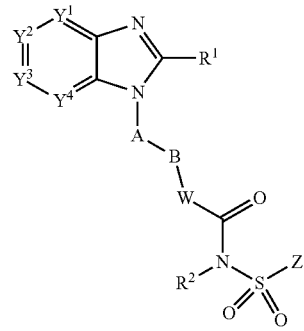

(I)

or a pharmaceutically acceptable salt thereof,
wherein
$Y^1$, $Y^2$, $Y^3$, and $Y^4$ are preferably independently selected from N, CH and C(L);
$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$ alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$ alkyl-C(O)—N($R^3$)—, $Q^1$-$C_{1-4}$ alkyl-N($R^3$)— or $C_{1-4}$ alkyl-C(O)—N($R^3$)—;

$Q^1$ is a 5 to 12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $R^3N(R^4)C$(=O)—, $C_{1-4}$ alkylsulfonylamino, $C_{3-7}$ cycloalkyl, $R^3C$(=O)N($R^4$)— or $NH_2(HN=)C$—;

A is a 5 or 6 membered monocyclic aromatic ring optionally containing up to 3 heteroatoms selected from O, N and S, wherein said 5 or 6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, acetyl, $R^3N(R^4)C$(=O)—, HO(O=)C—, $C_{1-4}$ alkyl-O(O=)C—, $C_{1-4}$ alkylsulfonylamino, $C_{3-7}$ cycloalkyl, $R^3C$(=O)N($R^4$)— and $NH_2(HN=)C$—;

B is halo-substituted $C_{1-6}$ alkylene, $C_{3-7}$ cycloalkylene, $C_{2-6}$ alkenylene, $C_{2-6}$ alkynylene, —O—$C_{1-5}$ alkylene, $C_{1-2}$ alkylene-O—$C_{1-2}$ alkylene or $C_{1-6}$ alkylene optionally substituted with an oxo group or $C_{1-3}$ alkyl;

W is NH, N—$C_{1-4}$ alkyl, O, S, N—$OR^5$ or a covalent bond;
$R^2$ is H, $C_{1-4}$ alkyl, OH or $C_{1-4}$ alkoxy;

Z is a 5 to 12 membered monocyclic or bicyclic aromatic ring optionally containing up to 3 heteroatoms selected from O, N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, $R^3C$(=O)N($R^4$)—, HO(O=)C—, $C_{1-4}$ alkyl-O(O=)C—, $C_{1-4}$ alkylsulfonylamino, $C_{3-7}$ cycloalkyl, $NH_2(HN=)C$—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, $C_{1-4}$ alkylthio, nitro, amino, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C$(=O)N($R^4$)—, $NH_2(HN=)C$—, $R^3N(R^4)C$(=O)—, $R^3N(R^4)S(O)m$-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;
$R^3$ and $R^4$ are independently selected from H and $C_{1-4}$ alkyl;
$R^5$ is H, $C_{1-4}$ alkyl, $C_{1-4}$ alkyl-(O=)C— or $C_{1-4}$ alkyl-O—(O=)—C—; and $Q^2$ is a 5 to 12 membered monocyclic or bicyclic aromatic ring, optionally containing up to 3 heteroatoms selected from O, N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C$(=O)N—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O)NH— or $NH_2(HN=)C$—.

In the compounds of formula (I),
$Y^1$, $Y^2$, $Y^3$, and $Y^4$ are preferably independently selected from N, CH and C(L);

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C$(=O)N($R^4$)—, $R^3N(R^4)C$(=O)—, $R^3N(R^4)S(O)m$-, $Q^2$, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;
$R^3$ and $R^4$ are independently selected from H and $C_{1-4}$ alkyl; and $Q^2$ is a 5 to 12 membered monocyclic or bicyclic aromatic ring, optionally containing up to 3 heteroatoms selected from O, N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C$(=O)N—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—.

More preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C$(=O)N($R^4$)—, $R^3N(R^4)C$(=O)—, $R^3N(R^4)S(O)m$-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;
$R^3$ and $R^4$ are independently selected from H and $C_{1-4}$ alkyl; and $Q^2$ is a 5 or 6 membered monocyclic aromatic ring, containing up to 3 heteroatoms selected from N and S, wherein said 5 or 6 membered monocyclic aromatic ring is optionally substituted with halo, more preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C$(=O)N($R^4$)—, $R^3N(R^4)C$(=O)—, $R^3N(R^4)S(O)m$-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;
$R^3$ and $R^4$ are independently selected from H and $C_{1-4}$ alkyl; and $Q^2$ is a 5 or 6 membered monocyclic aromatic ring, optionally containing 1 sulfur atom wherein said 5 or 6 membered monocyclic aromatic ring is optionally substituted with halo, more preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3N(R^4)C(=O)$—, $R^3N(R^4)S(O)m$—, $Q^2$-, $Q^2$-C(=O)—, $Q^2$-O—, $Q^2$-$C_{1-4}$alkyl-O—, or two adjacent L groups are joined together to form a methylenedioxy group;

m is 0, 1 or 2

$R^3$ and $R^4$ are independently selected from H and $C_{1-4}$ alkyl; and $Q^2$ is a 5 or 6 membered monocyclic aromatic ring system, more preferably $Y^1$, $Y^2$, $Y^3$, and $Y^4$ are independently selected from N, CH and C(L);

L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group, more preferably $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L);
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
m) $Y^1$, $Y^2$, $Y^3$ and $Y^4$ are CH;
n) $Y^1$ and $Y^2$ are C(L), $Y^3$ is CH and $Y^4$ is N;
o) $Y^1$, $Y^2$ and $Y^4$ are CH, and $Y^3$ is C(L);
p) $Y^1$ and $Y^2$ are C(L), $Y^3$ is N and $Y^4$ is CH;
q) $Y^1$ and $Y^3$ are C(L), and $Y^2$ and $Y^4$ are N;
r) $Y^1$ is C(L), $Y^2$ and $Y^3$ are CH, and $Y^4$ is N;
s) $Y^2$ is C(L), $Y^1$ and $Y^3$ are CH, and $Y^4$ is N; and
t) $Y^1$, $Y^2$ and $Y^3$ are C(L), and $Y^4$ is CH L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group, most preferably $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L); and
k) $Y^1$, $Y^2$ and $Y^3$ are C(L), and $Y^4$ is CH L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group.

In the compounds of Formula (I),
$R^1$ is preferably H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkyl, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—;

$Q^1$ is a 5 to 12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkylC(=O)—, HO(O=)C—, $C_{1-4}$ alkyl-O(O)C—, $R^3N(R^4)C(=O)$—, $C_{1-4}$ alkylsulfonylamino, $C_{3-7}$ cycloalkyl, $R^3C(=O)N(R^4)$— or NH$_2$(HN=)C—;

m is 0, 1 or 2; and $R^3$ and $R^4$ are independently selected from H and $C_{1-4}$ alkyl, In the compounds of Formula (I),
more preferably $R^1$ is H, $C_{1-8}$ alkyl, $C_{2-8}$ alkenyl, $C_{2-8}$ alkynyl, $C_{3-7}$ cycloalkyl, $Q^1$-, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(O)—, $Q^1$-O—, $Q^1$-S— or $Q^1$-$C_{1-4}$ alkyl-O—, or $C_{1-4}$alkyl-C(O)—N($R^3$)—;

$Q^1$ is a 5 to 12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkylC(=O)—;

m is 0, 1 or 2; and $R^3$ is H or $C_{1-4}$ alkyl,

In the compounds of Formula (I),
more preferably $R^1$ is H, $C_{1-8}$ alkyl, $C_{2-8}$ alkenyl, $C_{2-8}$ alkynyl, $C_{3-7}$ cycloalkyl, $Q^1$-, or mono- or di-($C_{1-8}$ alkyl) amino wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S—, $Q^1$-$C_{1-4}$ alkyl-O—, or $C_{1-4}$alkyl-C(O)—N(H)—;

$Q^1$ is a 5 or 6 membered monocyclic aromatic ring optionally containing up to 4 heteroatoms selected from N and S; and m is 0, 1 or 2, In the compounds of Formula (I),
more preferably $R^1$ is $C_{1-5}$ alkyl, $C_{3-7}$ cycloalkyl, or $Q^1$-, mono- or di-($C_{1-8}$ alkyl)amino wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$-, or $C_{1-4}$alkyl-C(O)—N(H)—; and $Q^1$ is a 5 to 12 membered monocyclic aromatic ring system optionally containing up to 2 heteroatoms selected from N and S, In the compounds of Formula (I),
more preferably $R^1$ is $C_{1-5}$ alkyl, mono- or di-($C_{1-8}$ alkyl) amino, pyrrolidinyl, or pyridyl optionally substituted with $C_{1-3}$ alkyl, hydroxy, oxo, a 5 or 6 membered monocyclic aromatic ring, wherein said 5 or 6 membered monocyclic aromatic ring contains 1 or 2 heteroatoms selected from N and S, or $C_{1-4}$alkyl-C(O)—N(H)—, In the compounds of Formula (I),
most preferably $R^1$ is methyl, ethyl, n-propyl, isopropyl, n-butyl, isobutyl, neopentyl, thiazolylethyl, methylamino, dimethylamino, pyrrolidinyl, pyridyl, or 1-acetylamino-1-methylethyl.

In the compounds of Formula (I), $R^2$ is preferably H or $C_{1-4}$ alkyl, most preferably H.

In the compounds of Formula (I), A is preferably a 5 or 6 membered monocyclic aromatic ring optionally containing up to 2 heteroatoms selected from O, N, and S, wherein said 5 or 6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy, more preferably 5 or 6 membered monocyclic aromatic ring optionally substituted with halo, $C_{1-4}$ alkyl or $C_{1-4}$ alkoxy, more preferably 5 or 6 membered monocyclic aromatic ring system optionally substituted with halo or $C_{1-4}$ alkyl, more preferably 5 or 6 membered monocyclic aromatic ring system, most preferably phenyl or pyridyl.

In the compounds of Formula (I), B is preferably $C_{3-7}$ cycloalkylene or $C_{1-6}$ alkylene optionally substituted with an oxo group or $C_{1-3}$ alkyl, more preferably $C_{1-3}$ alkylene optionally substituted with $C_{1-3}$ alkyl, more preferably $C_{1-2}$ alkylene optionally substituted with methyl, most preferably ethylene or propylene.

In the compounds of Formula (I), W is preferably NH, N—$C_{1-4}$ alkyl, O or N—OH, more preferably NH, N—$C_{1-2}$ alkyl or O, most preferably NH, N—$CH_3$ or O.

In the compounds of Formula (I), Z is preferably a 5 to 12 membered monocyclic or bicyclic aromatic ring optionally containing up to 3 heteroatoms selected from N, O, and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkylC(=O)—, $R^3$C(=O)N($R^4$)—, HO(O=)C—, $C_{1-4}$ alkyl-O(O=)C—, $C_{1-4}$ alkylsulfonylamino, $C_{1-4}$ alkyl-C(=O)NH—, $Q^2$-S(O)m-, $Q^2$-O—, $Q^2$-N($R^3$)— or $Q^2$-;
m is 0, 1 or 2;
$R^3$ and $R^4$ are independently selected from H and $C_{1-4}$ alkyl; and
$Q^2$ is a 5 to 12 membered monocyclic or bicyclic aromatic ring, optionally containing up to 3 heteroatoms selected from O, N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3$($R^4$)C(=O)N—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—, In the compounds of Formula (I),
more preferably Z is a 5 to 12 membered monocyclic or bicyclic aromatic ring optionally containing up to 3 heteroatoms selected from N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-;
m is 0, 1 or 2;
$R^3$ and $R^4$ are independently selected from H and $C_{1-4}$ alkyl; and $Q^2$ is a 5 or 6 membered monocyclic aromatic ring, containing up to 3 heteroatoms selected from N and S, wherein said 5 or 6 membered monocyclic aromatic ring is optionally substituted with halo, In the compounds of Formula (I),
more preferably Z is a 5 to 12 membered monocyclic or bicyclic aromatic ring optionally containing up to 3 heteroatoms selected from N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-;
m is 0, 1 or 2;
$R^3$ and $R^4$ are independently selected from H and $C_{1-4}$ alkyl; and
$Q^2$ is a 5 or 6 membered monocyclic aromatic ring or, optionally containing 1 sulfur atom wherein said 5 or 6 membered monocyclic aromatic ring is optionally substituted with halo, In the compounds of Formula (I),
more preferably Z is a 5 to 12 membered monocyclic or bicyclic aromatic ring optionally containing up to 3 heteroatoms selected from N and S, wherein said 5 to 12 membered monocyclic aromatic ring is optionally substituted with halo, $C_{1-4}$ alkyl, nitro, $R^3$C(=O)N($R^4$)— or $Q^2$-;
$R^3$ and $R^4$ are independently selected from H and $C_{1-4}$ alkyl; and
$Q^2$ is a 5 or 6 membered monocyclic aromatic ring system, more preferably Z is a 5 to 10 membered monocyclic or bicyclic aromatic ring optionally containing up to 3 heteroatoms selected from N and S, wherein said 5 to 10 membered monocyclic aromatic ring is optionally substituted with chloro, bromo, methyl, nitro, $CH_3$C(=O)NH—, tBuC(=O)NH— or phenyl, In the compounds of Formula (I),
most preferably Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl.

A preferred group of compounds of Formula (I) includes compounds wherein
$Y^1$, $Y^2$, $Y^3$, and $Y^4$ are independently selected from N, CH and C(L);
$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$alkyl-C(=O)—N($R^3$)—, or $C_{1-4}$alkyl-C(=O)—N($R^3$)—;
$Q^1$ is a 5 to 12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkylC(=O)—, HO(O=)C—, $C_{1-4}$ alkyl-O(O)C—, $R^3$N ($R^4$)C(=O)—, $C_{1-4}$ alkylsulfonylamino, $C_{3-7}$ cycloalkyl, $R^3$C(=O)N($R^4$)— or $NH_2$(HN=)C—;

A is a 5 or 6 membered monocyclic aromatic ring optionally containing up to 2 heteroatoms selected from O, N, and S, wherein said 5 or 6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5 to 12 membered monocyclic or bicyclic aromatic ring optionally containing up to 3 heteroatoms selected from N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkylC(=O)—, $R^3$C(=O)N($R^4$)—, HO(O=)C—, $C_{1-4}$ alkyl-O(O=)C—, $C_{1-4}$ alkylsulfonylamino, $C_{1-4}$ alkyl-C(=O)NH—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, $R^3$N($R^4$)C(=O)—, $R^3$N($R^4$)S(O)m-, $Q^2$, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl; and $Q^2$ is a 5 to 12 membered monocyclic or bicyclic aromatic ring, optionally containing up to 3 heteroatoms selected from O, N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3$($R^4$)C(=O)N—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—.

A further preferred group of compounds of Formula (I) includes compounds wherein $Y^1$, $Y^2$, $Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $Q^1$-, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(O)—, $Q^1$-O—, $Q^1$-S—, $Q^1$-$C_{1-4}$ alkyl-O—, or $C_{1-4}$alkyl-C(O)—N($R^3$)—;

$Q^1$ is a 5 to 12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkylC(=O)—;

A is a 5 or 6 membered monocyclic aromatic ring optionally substituted with halo, $C_{1-4}$ alkyl or $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5 to 12 membered monocyclic or bicyclic aromatic ring optionally containing up to 3 heteroatoms selected from N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, mono- or di-($C_{1-4}$ alkyl)amino, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, $R^3$N($R^4$)C(=O)—, $R^3$N($R^4$)S(O)m-, $Q^2$, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl; and $Q^2$ is a 5 or 6 membered monocyclic aromatic ring, containing up to 3 heteroatoms selected from N and S, wherein said 5 or 6 membered monocyclic aromatic ring is optionally substituted with halo.

A further preferred group of compounds of Formula (I) includes compounds wherein $Y^1$, $Y^2$, $Y^3$ and $Y^4$ are independently selected from N, CH and C(L);

$R^1$ is H, $C_{1-8}$ alkyl, $C_{2-8}$ alkenyl, $C_{2-8}$ alkynyl or $C_{3-7}$ cycloalkyl, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S—, $Q^1$-$C_{1-4}$ alkyl-O—, or $C_{1-4}$alkyl-C(O)—N($R^3$)—;

$Q^1$ is a 5 or 6 membered monocyclic aromatic ring optionally containing up to 4 heteroatoms selected from N and S;

A is a 5 or 6 membered monocyclic aromatic ring system optionally substituted with halo or $C_{1-4}$ alkyl;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5 to 12 membered monocyclic or bicyclic aromatic ring optionally containing up to 3 heteroatoms selected from N and S, wherein said 5 to 12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O), HO(O=)C—, $C_{1-4}$ alkyl-O(O=)C—, $C_{1-4}$ alkylsulfonylamino, $C_{3-7}$ cycloalkyl, $R^3$C(=O)N$R^4$—, $R^3$N($R^4$)C(=O)—, $R^3$N($R^4$)S(O)m-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl; and $Q^2$ is a 5 or 6 membered monocyclic aromatic ring or, optionally containing 1 sulfur atom wherein said 5 or 6 membered monocyclic aromatic ring is optionally substituted with halo.

A further preferred group of compounds of Formula (I) includes compounds wherein $Y^1$, $Y^2$, $Y^3$ and $Y^4$ are independently selected from N, CH and C(L);

$R^1$ is $C_{1-5}$ alkyl or $C_{3-7}$ cycloalkyl, wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$-, or $C_{1-4}$alkyl-C(O)—N(H)—;

$Q^1$ is a 5 to 12 membered monocyclic aromatic ring system optionally containing up to 2 heteroatoms selected from N and S, A is a 5 or 6 membered monocyclic aromatic ring system;

B is $C_{1-3}$ alkylene optionally substituted with $C_{1-3}$ alkyl;

W is NH, N—$C_{1-2}$ alkyl or O;

$R^2$ is H;

Z is a 5 to 12 membered monocyclic or bicyclic aromatic ring optionally containing up to 3 heteroatoms selected from N and S, wherein said 5 to 12 membered monocyclic aromatic ring is optionally substituted with halo, $C_{1-4}$ alkyl, nitro, $R^3C(=O)N(R^4)$— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3N(R^4)C(=O)$—, $R^3N(R^4)S(O)m$-, $Q^2$-, $Q^2$-C(=O)—, or two adjacent L groups are joined together to form a methylenedioxy group;

$R^3$ and $R^4$ are independently selected from H and $C_{1-4}$ alkyl; and $Q^2$ is a 5 or 6 membered monocyclic aromatic ring system.

A further preferred group of compounds of Formula (I) includes compounds wherein $Y^1$, $Y^2$, $Y^3$ and $Y^4$ are independently selected from N, CH and C(L);

$R^1$ is $C_{1-5}$ alkyl optionally substituted with $C_{1-3}$ alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$alkyl-C(O)—N($R^3$)—;

A is phenyl;

B is $C_{1-2}$ alkylene optionally substituted with methyl;

W is NH, N—CH$_3$ or O;

$R^2$ is H;

$R^3$ is H or $C_{1-4}$ alkyl;

Z is a 5 to 10 membered monocyclic or bicyclic aromatic ring optionally containing up to 3 heteroatoms selected from N and S, wherein said 5 to 10 membered monocyclic aromatic ring is optionally substituted with chloro, bromo, methyl, nitro, $CH_3C(=O)NH$—, $tBuC(=O)NH$— or phenyl; and L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group.

A further preferred group of compounds of Formula (I) includes compounds wherein $Y^1$, $Y^2$, $Y^3$ and $Y^4$ are independently selected from N, CH and C(L);

$R^1$ is methyl, ethyl, n-propyl, isopropyl, n-butyl, isobutyl, neopentyl, thiazolylethyl, methylamino, dimethylamino, pyrrolidinyl, pyridyl, or 1-acetylamino-1-methylethyl;

A is phenyl;

B is ethylene or propylene;

W is NH, N—CH$_3$ or O;

$R^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group.

A further preferred group of compounds of Formula (I) includes compounds wherein $Y^1$, $Y^2$, $Y^3$ and $Y^4$ are selected from the group consisting of
a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L);
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
m) $Y^1$, $Y^2$, $Y^3$ and $Y^4$ are CH;
n) $Y^1$ and $Y^2$ are C(L), $Y^3$ is CH and $Y^4$ is N;
o) $Y^1$, $Y^2$ and $Y^4$ are CH, and $Y^3$ is C(L);
p) $Y^1$ and $Y^2$ are C(L), $Y^3$ is N and $Y^4$ is CH;
q) $Y^1$ and $Y^3$ are C(L), and $Y^2$ and $Y^4$ are N;
r) $Y^1$ is C(L), $Y^2$ and $Y^3$ are CH, and $Y^4$ is N; and
s) $Y^2$ is C(L), $Y^1$ and $Y^3$ are CH, and $Y^4$ is N;

$R^1$ is methyl, ethyl, n-propyl, isopropyl, n-butyl, isobutyl, neopentyl, thiazolylethyl, methylamino, dimethylamino, pyrrolidinyl, pyridyl, or 1-acetylamino-1-methylethyl;

A is phenyl;

B is ethylene or propylene;

W is NH, N—CH$_3$ or O;

$R^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group.

A further preferred group of compounds of Formula (I) includes compounds wherein $Y^1$, $Y^2$, $Y^3$ and $Y^4$ are selected from the group consisting of
a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH; and
j) $Y^1$ and $Y^4$ are CH, and $Y^2$ and $Y^3$ are C(L);

$R^1$ is methyl, ethyl, n-propyl, isopropyl, n-butyl, isobutyl, neopentyl, thiazolylethyl, methylamino, dimethylamino, pyrrolidinyl, pyridyl, or 1-acetylamino-1-methylethyl;

A is phenyl;

B is ethylene or propylene;

W is NH, N—CH$_3$ or O;

R$^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group.

Preferred individual compounds of Formula (I) are as follows:

3-(4-{2-[({[(5-chloro-1,3-dimethyl-1H-pyrazol-4-yl)sulfonyl]amino}carbonyl)amino]ethyl}phenyl)-2-ethyl-5,7-dimethyl-3H-imidazo[4,5-b]pyridine;

3-(4-{2-[({[(2,4-dimethyl-1,3-thiazol-5-yl)sulfonyl]amino}carbonyl)amino]ethyl}phenyl)-2-ethyl-5,7-dimethyl-3H-imidazo[4,5-b]pyridine;

N-[5-({[({2-[4-(2-ethyl-5,7-dimethyl-3H-imidazo[4,5-b]pyridin-3-yl)phenyl]ethyl}amino)carbonyl]amino}sulfonyl)-1,3,4-thiadiazol-2-yl]acetamide;

6-ethyl-5-(4-{2-[({[(4-methylphenyl)sulfonyl]amino}carbonyl)amino]ethyl}phenyl)-5H-[1,3]dioxolo[4,5-f]benzimidazole;

6-chloro-5-cyano-2-ethyl-1-(4-{2-[({[(4-methylphenylsulfonyl]amino}carbonyl)amino]ethyl}phenyl)-1H-benzimidazole;

2-ethyl-5,7-dimethyl-3-(4-{2-[methyl({[(4-methylphenyl)sulfonyl]amino}carbonyl)amino]ethyl}phenyl)-3H-imidazo[4,5-b]pyridine;

2-ethyl-5,7-dimethyl-3-(4-{2-[({[(4-methylphenyl)sulfonyl]amino}carbonyl)amino]propyl}phenyl)-3H-imidazo[4,5-b]pyridine;

2-[4-(2-ethyl-5,7-dimethyl-3H-imidazo[4,5-b]pyridin-3-yl)phenyl]-1-methylethyl (4-methylphenyl)sulfonylcarbamate;

5,7-dimethyl-3-(4-{2-[({[(4-methylphenyl)sulfonyl]amino}carbonyl)amino]ethyl}phenyl)-2-propyl-3H-imidazo[4,5-b]pyridine;

2-isopropyl-5,7-dimethyl-3-(4-{2-[({[(4-methylphenyl)sulfonyl]amino}carbonyl)amino]ethyl}phenyl)-3H-imidazo[4,5-b]pyridine;

2-butyl-5,7-dimethyl-3-(4-{2-[({[(4-methylphenyl)sulfonyl]amino}carbonyl)amino]ethyl}phenyl)-3H-imidazo[4,5-b]pyridine;

2-isobutyl-5,7-dimethyl-3-(4-{2-[({[(4-methylphenyl)sulfonyl]amino}carbonyl)amino]ethyl}phenyl)-3H-imidazo[4,5-b]pyridine;

5,7-dimethyl-3-(4-{2-[({[(4-methylphenyl)sulfonyl]amino}carbonyl)amino]ethyl}phenyl)-2-neopentyl-3H-imidazo[4,5-b]pyridine;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

3-{4-[2-({[(4-biphenylsulfonyl)amino]carbonyl}amino)ethyl]phenyl}-2-ethyl-5,7-dimethyl-3H-imidazo[4,5-b]pyridine;

2-ethyl-5,7-dimethyl-3-{4-[2-({[(1-naphthylsulfonyl)amino}carbonyl)amino]ethyl]phenyl}-3H-imidazo[4,5-b]pyridine;

2-ethyl-5,7-dimethyl-3-{4-[2-({[(2-naphthylsulfonyl)amino}carbonyl)amino]ethyl]phenyl}-3H-imidazo[4,5-b]pyridine;

2-ethyl-5,7-dimethyl-3-(4-{2-[({[(2-thienyl)sulfonyl]amino}carbonyl)amino]ethyl}phenyl)-3H-imidazo[4,5-b]pyridine;

3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;

3-(4-{2-[({[(4,5-dichloro-2-thienyl)sulfonyl]amino}carbonyl)amino]ethyl}phenyl)-2-ethyl-5,7-dimethyl-3H-imidazo[4,5-b]pyridine;

3-{4-[2-({[(1-benzothien-2-ylsulfonyl)amino]carbonyl}amino)ethyl]phenyl}-2-ethyl-5,7-dimethyl-3H-imidazo[4,5-b]pyridine;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3H-imidazo[4,5-b]pyridine;

5-chloro-2-ethyl-7-methyl-3-(4-{2-[({[(4-methylphenyl)sulfonyl]amino}carbonyl)amino]ethyl}phenyl)-3H-imidazo[4,5-b]pyridine;

6-cyano-2-ethyl-5,7-dimethyl-3-(4-{2-[({[(4-methylphenyl)sulfonyl]amino}carbonyl)amino]ethyl}phenyl)-3H-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;

4-methyl-2-ethyl-3-(4-{2-[({[(4-methylphenyl)sulfonyl]amino}carbonyl)amino]ethyl}phenyl)benzimidazole;

7-chloro-2-ethyl-3-(4-{2-[({[(4-methylphenyl)sulfonyl]amino}carbonyl)amino]ethyl}phenyl)benzimidazole;

5-methoxy-2-ethyl-3-(4-{2-[({[(4-methylphenyl)sulfonyl]amino}carbonyl)amino]ethyl}phenyl)benzimidazole;

5-acetyl-2-ethyl-3-(4-{2-[({[(4-methylphenyl)sulfonyl]amino}carbonyl)amino]ethyl}phenyl)benzimidazole;

5-cyano-2-ethyl-1-(4-{2-[({[(4-methylphenyl)sulfonyl]amino}carbonyl)amino]ethyl}phenyl)-1H-benzimidazole;

2-ethyl-5-hydroxy-1-(4-{2-[({[(4-methylphenyl)sulfonyl]amino}carbonyl)amino]ethyl}phenyl)-1H-benzimidazole;

2-ethyl-4,5-dimethyl-1-(4-{2-[({[(4-methylphenyl)sulfonyl]amino}carbonyl)amino]ethyl}phenyl)-1H-benzimidazole;

4,6-dimethyl-2-ethyl-3-(4-{2-[({[(4-methylphenyl)sulfonyl]amino}carbonyl)amino]ethyl}phenyl)benzimidazole;

5,6-dimethyl-1-(4-{2-[({[(4-methylphenyl)sulfonyl]amino}carbonyl)amino]ethyl}phenyl)-1H-benzimidazole;

5,6-dichloro-2-ethyl-1-(4-{2-[({[(4-methylphenyl)sulfonyl]amino}carbonyl)amino]ethyl}phenyl)-1H-benzimidazole;

2-[4-(5,6-dichloro-2-ethyl-1H-benzimidazol-1-yl)phenyl]ethyl-(4-methylphenyl)sulfonylcarbamate;

6-chloro-5-trifluoromethyl-1-(4-{2-[({[(4-methylphenyl)sulfonyl]amino}carbonyl)amino]ethyl}phenyl)-1H-benzimidazole;

4-(6-chloro-2-ethyl-5-trifluoromethyl-1H-benzimidazol-1-yl)phenethyl-(4-methylphenyl)sulfonylcarbamate;

5-chloro-6-methyl-1-(4-{2-[({[(4-methylphenyl)sulfonyl]amino}carbonyl)amino]ethyl}phenyl)-1H-benzimidazole;

6-chloro-2-ethyl-1-(4-{2-[({[(4-methylphenyl)sulfonyl]amino}carbonyl)amino]ethyl}phenyl)-1H-benzimidazole-5-carboxamide;

2-ethyl-3-{4-[2-({[({3-[hydroxy(oxido)amino]phenyl}sulfonyl)amino]carbonyl}amino)ethyl]phenyl}-5,7-dimethyl-3H-imidazo[4,5-b]pyridine;

3-(4-{2-[({[(4-chlorophenyl)sulfonyl]amino}carbonyl)amino]ethyl}phenyl)-2-ethyl-5,7-dimethyl-3H-imidazo[4,5-b]pyridine;

n-[4-({[({2-[4-(2-ethyl-5,7-dimethyl-3H-imidazo[4,5-b]pyridin-3-yl)phenyl]ethyl}amino)carbonyl]amino}sulfonyl)phenyl]-2,2-dimethylpropanamide;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

3-(4-{2-[({[(3-chlorophenyl)sulfonyl]amino}carbonyl)amino]ethyl}phenyl)-2-ethyl-5,7-dimethyl-3H-imidazo[4,5-b]pyridine;

3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;

3-(4-{2-[({[(5-bromo-2-thienyl)sulfonyl]amino}carbonyl)amino]ethyl}phenyl)-2-ethyl-5,7-dimethyl-3H-imidazo[4,5-b]pyridine;

3-(4-{2-[({[(2-bromophenyl)sulfonyl]amino}carbonyl)amino]ethyl}phenyl)-2-ethyl-5,7-dimethyl-3H-imidazo[4,5-b]pyridine;

3-{4-[2-({[({4-chloro-3-nitrophenyl}sulfonyl)amino]carbonyl}amino)ethyl]phenyl}-2-ethyl-5,7-dimethyl-3H-imidazo[4,5-b]pyridine;

2-[4-(2-ethyl-4,6-dimethyl-1H-imidazo[4,5-c]pyridin-1-yl)phenyl]ethyl (4-methylphenyl)sulfonylcarbamate;

2-{4-[5,7-dimethyl-2-(methylamino)-3H-imidazo[4,5-b]pyridin-3-yl]phenyl}ethyl (4-methylphenyl)sulfonylcarbamate;

N-{[(2-{4-[5,7-dimethyl-2-(methylamino)-3H-imidazo[4,5-b]pyridin-3-yl]phenyl}ethyl)amino]carbonyl}-4-methylbenzenesulfonamide;

N-{[(2-{4-[2-ethyl-5-(1-hydroxy-1-methylethyl)-1H-benzimidazol-1-yl]phenyl}ethyl)amino]carbonyl}-4-methylbenzenesulfonamide;

2-ethyl-4,6-dimethyl-1-(4-{2-[({[(4-methylphenyl)sulfonyl]amino}carbonyl)amino]ethyl}phenyl)-1H-benzimidazole-5-carboxamide;

2-{4-[6-chloro-2-ethyl-5-(trifluoromethyl)-1H-benzimidazol-1-yl]phenyl}ethyl (2-chlorophenyl)sulfonylcarbamate;

2-{5-[6-chloro-2-ethyl-5-(trifluoromethyl)-1H-benzimidazol-1-yl]-2-pyridinyl}ethyl (4-methylphenyl)sulfonylcarbamate;

2-{4-[6-chloro-2-ethyl-5-(trifluoromethyl)-1H-benzimidazol-1-yl]phenyl}ethyl (5-methyl-2-pyridinyl)sulfonylcarbamate;

2-{4-[6-chloro-2-(1H-pyrazol-3-yl)-5-(trifluoromethyl)-1H-benzimidazol-1-yl]phenyl}ethyl (4-methylphenyl)sulfonylcarbamate;

2-{4-[6-chloro-2-(4-pyridinyl)-5-(trifluoromethyl)-1H-benzimidazol-1-yl]phenyl}ethyl (4-methylphenyl)sulfonylcarbamate;

2-{4-[5-(aminocarbonyl)-6-chloro-2-ethyl-1H-benzimidazol-1-yl]phenyl}ethyl (4-methylphenyl)sulfonylcarbamate;

N-{[(2-{4-[6-chloro-2-ethyl-5-(methylsulfonyl)-1H-benzimidazol-1-yl]phenyl}ethyl)amino]carbonyl}-4-methylbenzenesulfonamide;

2-{4-[6-chloro-2-ethyl-5-(methylsulfonyl)-1H-benzimidazol-1-yl]phenyl}ethyl (4-methylphenyl)sulfonylcarbamate;

N-[({2-[4-(2-ethyl-5,7-dimethyl-3H-imidazo[4,5-b]pyridin-3-yl)phenyl]ethyl}amino)carbonyl]-2-thiophenesulfonamide;

2-[4-(4,6-dimethyl-2-phenyl-1H-imidazo[4,5-c]pyridin-1-yl)phenyl]ethyl (4-methylphenyl)sulfonylcarbamate;

2-[4-(2-butyl-4,6-dimethyl-1H-imidazo[4,5-c]pyridin-1-yl)phenyl]ethyl (4-methylphenyl)sulfonylcarbamate;

2-{4-[6-chloro-2-ethyl-5-(trifluoromethyl)-1H-benzimidazol-1-yl]phenyl}ethyl (5-chloro-1,3-dimethyl-1H-pyrazol-4-yl)sulfonylcarbamate;

2-{4-[4,6-dimethyl-2-(3-phenylpropyl)-1H-imidazo[4,5-c]pyridin-1-yl]phenyl}ethyl (4-methylphenyl)sulfonylcarbamate;

2-{4-[6-chloro-2-(2-pyridinyl)-5-(trifluoromethyl)-1H-benzimidazol-1-yl]phenyl}ethyl (4-methylphenyl)sulfonylcarbamate;

(1S)-2-{4-[6-chloro-2-ethyl-5-(trifluoromethyl)-1H-benzimidazol-1-yl]phenyl}-1-methylethyl (4-methylphenyl)sulfonylcarbamate;

2-{6-[6-chloro-2-ethyl-5-(trifluoromethyl)-1H-benzimidazol-1-yl]-3-pyridinyl}ethyl (4-methylphenyl)sulfonylcarbamate;

N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide;

N-{[(2-{4-[5,7-dimethyl-2-(1H-pyrazol-3-yl)-3H-imidazo[4,5-b]pyridin-3-yl]phenyl}ethyl)amino]carbonyl}-4-methylbenzenesulfonamide;

2-{4-[2-(1,1-dimethylethyl)-4,6-dimethyl-1H-imidazo[4,5-c]pyridin-1-yl]phenyl}ethyl (4-methylphenyl)sulfonylcarbamate;

2-{4-[2-[1-(acetylamino)-1-methylethyl]-6-chloro-5-(trifluoromethyl)-1H-benzimidazol-1-yl]phenyl}ethyl (4-methylphenyl)sulfonylcarbamate;

6-chloro-2-ethyl-1-(4-{2-[methyl({[(4-methylphenyl)sulfonyl]amino}carbonyl)amino]ethyl}phenyl)-1H-benzimidazole-5-carboxamide; and salts thereof.

Most preferred individual compounds of Formula (I) are following:

6-ethyl-5-(4-{2-[({[(4-methylphenyl)sulfonyl]amino}carbonyl)amino]ethyl}phenyl)-5H-[1,3]dioxolo[4,5-f]benzimidazole;

6-chloro-5-cyano-2-ethyl-1-(4-{2-[({[(4-methyl phenylsulfonyl]amino}carbonyl)amino]ethyl}phenyl)-1H-benzimidazole;

2-[4-(2-ethyl-5,7-dimethyl-3H-imidazo[4,5-b]pyridin-3-yl)phenyl]-1-methylethyl (4-methylphenyl)sulfonylcarbamate;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

2-ethyl-5,7-dimethyl-3-(4-{2-[({[(2-thienyl)sulfonyl]amino}carbonyl)amino]ethyl}phenyl)-3H-imidazo[4,5-b]pyridine;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3H-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;
5-methoxy-2-ethyl-3-(4-{2-[({[(4-methylphenyl)sulfonyl]amino}carbonyl)amino]ethyl}phenyl)benzimidazole;
5-acetyl-2-ethyl-3-(4-{2-[({[(4-methylphenyl)sulfonyl]amino}carbonyl)amino]ethyl}phenyl)benzimidazole;
5-cyano-2-ethyl-1-(4-{2-[({[(4-methylphenyl)sulfonyl]amino}carbonyl)amino]ethyl}phenyl)-1H-benzimidazole;
2-ethyl-5-hydroxy-1-(4-{2-[({[(4-methylphenyl)sulfonyl]amino}carbonyl)amino]ethyl}phenyl)-1H-benzimidazole;
2-ethyl-4,5-dimethyl-1-(4-{2-[({[(4-methylphenyl)sulfonyl]amino}carbonyl)amino]ethyl}phenyl)-1H-benzimidazole;
4-(6-chloro-2-ethyl-5-trifluoromethyl-1H-benzimidazol-1-yl)phenethyl-(4-methylphenyl)sulfonylcarbamate; and
6-chloro-2-ethyl-1-(4-{2-[({[(4-methylphenyl)sulfonyl]amino}carbonyl)amino]ethyl}phenyl)-1H-benzimidazole-5-carboxamide;
2-[4-(2-ethyl-4,6-dimethyl-1H-imidazo[4,5-c]pyridin-1-yl)phenyl]ethyl (4-methylphenyl)sulfonylcarbamate;
2-{4-[5,7-dimethyl-2-(methylamino)-3H-imidazo[4,5-b]pyridin-3-yl]phenyl}ethyl (4-methylphenyl)sulfonylcarbamate;
N-{[(2-{4-[5,7-dimethyl-2-(methylamino)-3H-imidazo[4,5-b]pyridin-3-yl]phenyl}ethyl)amino]carbonyl}-4-methylbenzenesulfonamide;
N-{[(2-{4-[2-ethyl-5-(1-hydroxy-1-methylethyl)-1H-benzimidazol-1-yl]phenyl}ethyl)amino]carbonyl}-4-methylbenzenesulfonamide;
2-ethyl-4,6-dimethyl-1-(4-{2-[({[(4-methylphenyl)sulfonyl]amino}carbonyl)amino]ethyl}phenyl)-1H-benzimidazole-5-carboxamide;
2-{4-[6-chloro-2-ethyl-5-(trifluoromethyl)-1H-benzimidazol-1-yl]phenyl}ethyl (2-chlorophenyl)sulfonylcarbamate;
2-{5-[6-chloro-2-ethyl-5-(trifluoromethyl)-1H-benzimidazol-1-yl]-2-pyridinyl}ethyl (4-methylphenyl)sulfonylcarbamate;
2-{4-[6-chloro-2-ethyl-5-(trifluoromethyl)-1H-benzimidazol-1-yl]phenyl}ethyl (5-methyl-2-pyridinyl)sulfonylcarbamate;
2-{4-[6-chloro-2-(1H-pyrazol-3-yl)-5-(trifluoromethyl)-1H-benzimidazol-1-yl]phenyl}ethyl (4-methylphenyl)sulfonylcarbamate;
2-{4-[6-chloro-2-(4-pyridinyl)-5-(trifluoromethyl)-1H-benzimidazol-1-yl]phenyl}ethyl (4-methylphenyl)sulfonylcarbamate;
2-{4-[5-(aminocarbonyl)-6-chloro-2-ethyl-1H-benzimidazol-1-yl]phenyl}ethyl (4-methylphenyl)sulfonylcarbamate;
N-{[(2-{4-[6-chloro-2-ethyl-5-(methylsulfonyl)-1H-benzimidazol-1-yl]phenyl}ethyl)amino]carbonyl}-4-methylbenzenesulfonamide;
2-{4-[6-chloro-2-ethyl-5-(methylsulfonyl)-1H-benzimidazol-1-yl]phenyl}ethyl (4-methylphenyl)sulfonylcarbamate;
N-[({2-[4-(2-ethyl-5,7-dimethyl-3H-imidazo[4,5-b]pyridin-3-yl)phenyl]ethyl}amino)carbonyl]-2-thiophenesulfonamide;
2-[4-(4,6-dimethyl-2-phenyl-1H-imidazo[4,5-c]pyridin-1-yl)phenyl]ethyl (4-methylphenyl)sulfonylcarbamate;
2-[4-(2-butyl-4,6-dimethyl-1H-imidazo[4,5-c]pyridin-1-yl)phenyl]ethyl (4-methylphenyl)sulfonylcarbamate;
2-{4-[6-chloro-2-ethyl-5-(trifluoromethyl)-1H-benzimidazol-1-yl]phenyl}ethyl (5-chloro-1,3-dimethyl-1H-pyrazol-4-yl)sulfonylcarbamate;
2-{4-[4,6-dimethyl-2-(3-phenylpropyl)-1H-imidazo[4,5-c]pyridin-1-yl]phenyl}ethyl (4-methylphenyl)sulfonylcarbamate;
2-{4-[6-chloro-2-(2-pyridinyl)-5-(trifluoromethyl)-1H-benzimidazol-1-yl]phenyl}ethyl (4-methylphenyl)sulfonylcarbamate;
(1S)-2-{4-[6-chloro-2-ethyl-5-(trifluoromethyl)-1H-benzimidazol-1-yl]phenyl}-1-methylethyl (4-methylphenyl)sulfonylcarbamate;
2-{6-[6-chloro-2-ethyl-5-(trifluoromethyl)-1H-benzimidazol-1-yl]-3-pyridinyl}ethyl (4-methylphenyl)sulfonylcarbamate;
N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide;
N-{[(2-{4-[5,7-dimethyl-2-(1H-pyrazol-3-yl)-3H-imidazo[4,5-b]pyridin-3-yl]phenyl}ethyl)amino]carbonyl}-4-methylbenzenesulfonamide;
2-{4-[2-(1,1-dimethylethyl)-4,6-dimethyl-1H-imidazo[4,5-c]pyridin-1-yl]phenyl}ethyl (4-methylphenyl)sulfonylcarbamate;
2-{4-[2-[1-(acetylamino)-1-methylethyl]-6-chloro-5-(trifluoromethyl)-1H-benzimidazol-1-yl]phenyl}ethyl (4-methylphenyl)sulfonylcarbamate;
6-chloro-2-ethyl-1-(4-{2-[methyl({[(4-methylphenyl)sulfonyl]amino}carbonyl)amino]ethyl}phenyl)-1H-benzimidazole-5-carboxamide; and salts thereof.

In another preferred aspect, the EP4 receptor ligand (antagonist), which is disclosed in WO 2005/021508, is phenyl or pyridyl amide compounds of the following Formula (II) or pharmaceutically acceptable salts thereof, {Chem. 10}

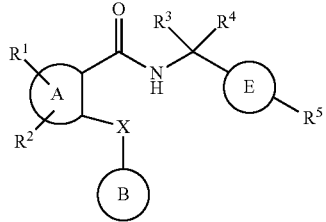

(II)

wherein A represents a phenyl group or a pyridyl group; B represents an aryl group or a heteroaryl group;

E represents a 1,4-phenylene group;

$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

$R^3$ and $R^4$ independently represent a hydrogen atom or an alkyl group having from 1 to 4 carbon atoms; or $R^3$ and $R^4$ may be joined together to form an alkylene chain having 2 to 6 carbon atoms;

$R^5$ represents —$CO_2H$, $CO_2W$,

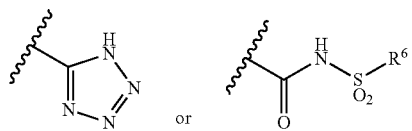

{Chem. 11} or ;

$R^6$ represents an alkyl group having from 1 to 6 carbon atoms, a cycloalkyl group having from 3 to 7 ring atoms, an aryl group or a heteroaryl group;

X represents a methylene group, an oxygen atom or a sulfur atom;

said aryl groups have from 6 to 10 carbon atoms; said heteroaryl groups are 5 to 10-membered aromatic heterocyclic groups containing from 1 to 3 heteroatoms selected from the group consisting of sulfur atom, oxygen atom and nitrogen atom;

said aryl groups and said heteroaryl groups referred to in the definitions of B are unsubstituted or are substituted by at least one substituent selected from the group consisting of substituents alpha;

said 1,4-phenylene group referred to in the definition of E is unsubstituted or is substituted by at least one substituent selected from the group consisting of substituents beta;

said aryl groups and said heteroaryl groups referred to in the definitions of $R^6$ and alpha are unsubstituted or are substituted by at least one substituent selected from the group consisting of substituents beta;

said substituents alpha are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent alpha groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl (alkyl) amino groups having from 1 to 6 carbon atoms, alkanoylaminoalkyl groups having from 1 to 6 carbon atoms in both the alkanoyl and alkyl part, alkanoyl (alkyl) aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms; said substituents beta are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

W is a pharmaceutically acceptable ester prodrug group; with the proviso $R^1$ and $R^2$ do not represent a hydrogen atom simultaneously.

In the compounds of Formula (II),

B preferably represents an aryl or heteroaryl group such as phenyl, naphthyl, pyridyl, quinolyl or isoquinolyl. B is preferably unsubstituted or is substituted by at least one substituent selected from the group consisting of substituents alpha; said substituents alpha are selected from the group consisting halogen atoms (e.g. fluoro, chloro), alkyl groups having from 1 to 4 carbon atoms (e.g. methyl, ethyl), alkoxy groups having from 1 to 4 carbon atoms (e.g. methoxy), haloalkoxy groups having from 1 to 4 carbon atoms (e.g. trifluoromethoxy), cyano groups, alkynyl groups having from 2 to 6 carbon atoms (e.g. ethynyl), alkanoyl groups having from 1 to 5 carbon atoms (e.g. acetyl), cycloalkyl groups having from 3 to 7 ring atoms (e.g. cyclopentyl), heteroaryl groups (e.g. 2-, 3- or 4-pyridyl, 1-methylimidazol-2-yl, thiazol-2-yl, 2-methylthiazol-4-yl), aryl groups (e.g. phenyl), aralkoxy groups having from 7 to 10 carbon atoms (e.g. benzyloxy), arylcarbonyl groups (e.g. benzoyl), two adjacent alpha groups are optionally joined together to form an alkylene chain having 3 carbon atoms, alkylthio groups having from 1 to 4 carbon atoms (e.g. methylthio) and di-alkylaminoalkyl groups having from 1 to 6 carbon atoms in the alkyl part; said heteroaryl groups referred to in the definitions of alpha are unsubstituted or are substituted by alkyl groups having from 1 to 4 carbon atoms (e.g. methyl). In the definition of B, aryl is preferably phenyl or naphthyl and heteroaryl is a 5- to 10-membered aromatic heterocyclic group containing either from 1 to 3 nitrogen heteroatoms, or 1 or 2 nitrogen heteroatoms and/or 1 oxygen or 1 sulphur heteroatom.

More preferably B represents a phenyl group optionally substituted by substituent selected from the group consisting of substituents alpha; said substituents alpha are selected from the group consisting of halogen atoms (e.g. fluoro, chloro), alkyl groups having from 1 to 4 carbon atoms (e.g. methyl, ethyl), alkoxy groups having from 1 to 4 carbon atoms (e.g. methoxy), haloalkoxy groups having from 1 to 4 carbon atoms (e.g. trifluoromethoxy), cyano groups, alkynyl groups having from 2 to 6 carbon atoms (e.g. ethynyl), alkanoyl groups having from 1 to 4 carbon atoms (e.g. acetyl), cycloalkyl groups having from 3 to 7 ring atoms (e.g. cyclopentyl), alkylthio groups having from 1 to 4 carbon atoms (e.g. methylthio), di-alkylaminoalkyl groups having from 1 to 6 carbon atoms in the alkyl part, thiazolyl groups, isothiazolyl groups, oxazolyl groups, isoxazolyl groups, imidazolyl groups, pyridyl groups, benzyloxy groups, phenyl groups or benzoyl groups; said thiazolyl groups, isothiazolyl groups, oxazolyl groups, isoxazolyl groups, imidazolyl groups and pyridyl groups referred to in the definitions of alpha are unsubstituted or are substituted by alkyl groups having from 1 to 4 carbon atoms. More preferably B represents a phenyl group optionally substituted by substituent selected from the group consisting of substituents alpha; said substituents alpha are selected from the group consisting of fluorine atoms, chlorine atoms, methyl groups, ethyl groups, methoxy groups, trifluoromethoxy groups, cyano groups, ethynyl groups, acetyl groups, cyclopentyl groups, methylthio groups, dimethylaminoethyl groups, phenyl groups, imidazolyl groups optionally substituted by methyl groups, thiazolyl groups optionally substituted by methyl groups, pyridyl groups or benzyloxy groups. More preferably, B represents a phenyl group substituted by 1 or 2 fluoro or chloro substituents. More preferably, B represents a phenyl group substituted by 1 fluoro or chloro substituent.

Most preferably, B represents 3-fluorophenyl.

In the compounds of Formula (II),

X preferably represents a methylene group or an oxygen atom. More preferably, X represents an oxygen atom.

In the compounds of Formula (II), preferably, $R^1$ and $R^2$ independently represent a hydrogen atom, a fluorine atom, a chlorine atom, trifluoromethyl, cyano or aminocarbonyl. More preferably, $R^1$ represents a halogen atom (e.g. fluoro, chloro) and $R^2$ represents a hydrogen atom.

In the compounds of Formula (II), preferably, $R^3$ and $R^4$ independently represent a hydrogen atom or an alkyl group having from 1 to 4 carbon atoms (e.g. methyl, ethyl). More preferably $R^3$ represents an alkyl group having from 1 to 4 carbon atoms (e.g. methyl, ethyl) and $R^4$ represents a hydrogen atom. Most preferably $R^3$ represents a methyl group and $R^4$ represents a hydrogen atom.

In the compounds of Formula (II), $R^5$ preferably represents —CO$_2$H,

{Chem. 12}

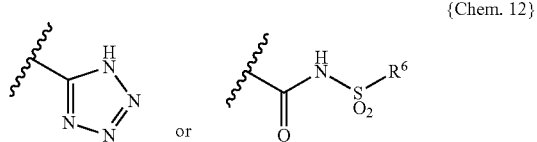

and $R^6$ preferably represents an aryl group optionally substituted by halogen atoms or is a heteroaryl group. More preferably, $R^5$ represents —CO$_2$H, {Chem. 13}

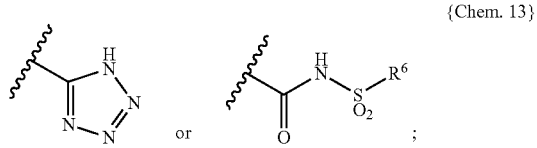

and $R^6$ represents an aryl group optionally substituted by halogen atoms. More preferably $R^6$ represents methyl, cyclohexyl, phenyl group optionally substituted by halogen atoms (such as 2-, 3- or 4-chlorophenyl, 3-fluorophenyl), 3-methylphenyl, 3-methoxyphenyl or 5-methyl-2-pyridyl. Further more preferably $R^5$ represents —CO$_2$H or {Chem. 14}

Most preferably $R^5$ represents —CO$_2$H.

Particularly preferred compounds of the invention include those in which each variable in Formula (II) is selected from the preferred groups for each variable.

Even more preferable compounds of the invention include those where each variable in Formula (II) is selected from the more preferred groups for each variable.

A preferred individual compound of Formula (II) is selected from 4-((1S)-1-{[5-chloro-2-(4-flurophenoxy)benzoyl]amino} ethyl) benzoic acid; 4-[(1S)-1-({[5-chloro-2-(4-fluorophenoxy) pyridin-3-yl] carbonyl} amino) ethyl] benzoic acid; 4-[(1S)-1-({[5-chloro-2-(3-cyanophenoxy) pyridin-3-yl] carbonyl} amino) ethyl]benzoic acid; 4-[(1S)-1-({[5-chloro-2-(3-fluorophenoxy) pyridin-3-yl] carbonyl} amino) ethyl] benzoic acid; 4-[(1S)-1-({[5-chloro-2-(3-chlorophenoxy)pyridin-3-yl]carbonyl}amino) ethyl] benzoic acid; 4-[(1S)-1-({[5-chloro-2-(3-fluorophenoxy)benzoyl] amino} ethyl) benzoic acid; 4-[(1S)-1-({[5-chloro-2-(3-methoxyphenoxy)benzoyl]amino} ethyl) benzoic acid; 4-((1S)-1-{[5-chloro-2-(3-chlorophenoxy) benzoyl] amino} ethyl) benzoic acid; 4-[(1S)-1-({[5-chloro-2-(2,4-difluorophenoxy) pyridin-3-yl] carbonyl} amino) ethyl] benzoic acid; 4-[(1S)-1-({[5-chloro-2-(4-chloro-3-fluorophenoxy) pyridin-3-yl] carbonyl} amino) ethyl] benzoic acid; 4-[(1S)-1-({[5-chloro-2-(2-chloro-4-fluorophenoxy) pyridin-3-yl] carbonyl} amino) ethyl] benzoic acid; 4-[(1S)-1-({[5-chloro-2-(2,6-difluorophenoxy) pyridin-3-yl] carbonyl} amino) ethyl] benzoic acid; 4-[(1S)-1-({[5-chloro-2-(3,4-difluorophenoxy) pyridin-3-yl] carbonyl} amino) ethyl] benzoic acid; 4-{(1S)-1-[({5-chloro-2-[3-(1,3-thiazol-2-yl) phenoxy] pyridin-3-yl} carbonyl) amino] ethyl} benzoic acid; 4-[(1S)-1-({[5-chloro-2-(2,3-difluorophenoxy) pyridin-3-yl] carbonyl} amino) ethyl] benzoic acid; 4-[(1S)-1-({[5-chloro-2-(2,5-difluorophenoxy)pyridin-3-yl] carbonyl} amino) ethyl]benzoic acid; 4-[(1S)-1-({[5-chloro-2-(4-chlorophenoxy) pyridin3-yl] carbonyl}amino) ethyl] benzoic acid; 4-[(1S)-1-({[5-chloro-2-(4-chloro-2-fluorophenoxy) pyridin-3-yl] carbonyl} amino) ethyl] benzoic acid; 4-[(S)-1-({[5-chloro-2-(2-chloro-5-fluorophenoxy) pyridin-3-yl] carbonyl} amino) ethyl] benzoic acid; 4-[(1S)-1-({[5-chloro-2-(3-methylphenoxy) pyridin-3-yl] carbonyl} amino) ethyl]benzoic acid; 4-[(1S)-1-({[5-chloro-2-(4-fluoro-3-methylphenoxy) pyridin-3-yl]carbonyl} amino) ethyl] benzoic acid; 4-[(1S)-1-({[5-chloro-2-(3,5-difluorophenoxy) pyridin-3-yl] carbonyl} amino) ethyl] benzoic acid; 4-((1S)-1-{[5-chloro-2-(2,3-difluorophenoxy) benzoyl] amino} ethyl) benzoic acid; 4-((1S)-1-{[5-chloro-2-(2,4-difluorophenoxy)benzoyl]amino}ethyl) benzoic acid; 4-((1S)-1-{[5-chloro-2-(3,4-difluorophenoxy) benzoyl] amino} ethyl) benzoic acid; 4-[(1S)-1-({[5-chloro-2-(3-chloro-5-fluorophenoxy) pyridin-3-yl] carbonyl} amino) ethyl] benzoic acid; 4-[(1S)-1-({[5-chloro-2-(3-chloro-2-methylphenoxy) pyridin-3-yl] carbonyl} amino) ethyl] benzoic acid; 4-((1S)-1-{[5-chloro-2-(3,5-difluorophenoxy) benzoyl] amino} ethyl) benzoic acid; 4-((1S)-1-{[5-chloro-2-(2,5-difluorophenoxy) benzoyl] amino} ethyl) benzoic acid; 4-[(1S)-1-({[5-chloro-2-(3-chloro-2-fluorophenoxy) pyridin-3-yl] carbonyl} amino) ethyl]benzoic acid; 4-[(1S)-1-({[5-chloro-2-(3-pyridin-2-ylphenoxy) pyridin-3-yl]carbonyl} amino) ethyl] benzoic acid; 4-[(1S)-1-({[5-chloro-2-(4-pyridin-2-ylphenoxy)pyridin-3-yl] carbonyl} amino) ethyl] benzoic acid; 4-[(1S)-1-({[5-chloro-2-(4-pyridin-4-ylphenoxy)pyridin-3-yl] carbonyl} amino) ethyl] benzoic acid; 4-[(1S)-1-({[5-chloro-2-(3-chloro-5-methylphenoxy) pyridin-3-yl] carbonyl} amino) ethyl] benzoic acid; 4-((1S)-1-{[5-chloro-2-(3-methylphenoxy) benzoyl] amino} ethyl) benzoic acid; 4-((1S)-1-{[5-chloro-2-(3-chloro-5-fluorophenoxy)benzoyl]amino} ethyl) benzoic acid; 4-((1S)-1-{[5- chloro-2-(2,6-difluorophenoxy) benzoyl] amino} ethyl) benzoic acid; 4-((1S)-1-{[5-chloro-2-phenoxypyridin-3-yl) carbonyl] amino} ethyl) benzoic acid; 4-[(1S)-1-({[5-chloro-2-(2,3-dimethylphenoxy) pyridin-3-yl] carbonyl} amino) ethyl] benzoic acid; 4-[(1S)-1-({[5-chloro-2-(2,3-dichlorophenoxy) pyridin-3-yl]carbonyl) amino) ethyl] benzoic acid; 4-[(1S)-1-({[5-chloro-2-(3,4-dichlorophenoxy) pyridin-3-yl] carbonyl} amino) ethyl] benzoic acid; 4-[(1S)-1-({[5-chloro-2-(3,5-dichlorophenoxy) pyridin-3-yl] carbonyl} amino) ethyl]benzoic acid; and 4-[(1S)-1-({[5-chloro-2-(3-fluoro-4-methylphenoxy) pyridin-3-yl] carbonyl} amino) ethyl] benzoic acid; or a pharmaceutically acceptable salt thereof.

A further preferred individual compound of Formula (II) is selected from 4-((1S)-1-{[5-chloro-2-(4-fluorophenoxy) benzoyl]amino} ethyl) benzoic acid; 4-[(1S)-1-({[5-chloro-2-(4-fluorophenoxy)pyridin-3-yl]carbonyl}amino) ethyl] benzoic acid; 4-[(1S)-1-({[5-chloro-2-(3-cyanophenoxy) pyridin-3-yl]carbonyl} amino) ethyl] benzoic acid; 4-[(1S)-1-({[5-chloro-2-(3-fluorophenoxy)pyridin-3-yl] carbonyl}amino) ethyl] benzoic acid; 4-[(1S)-1-({[5-chloro-2-(3-chlorophenoxy) pyridin-3-yl] carbonyl} amino) ethyl] benzoic acid; 4-((1S)-1-{[5-chloro-2-(3-fluorophenoxy) benzoyl] amino} ethyl) benzoic acid; 4-((1S)-1-{[5-chloro-2-(3-chlorophenoxy) benzoyl] amino} ethyl) benzoic acid; 4-[(1S)-1-({[5-chloro-2-(2-chloro-4-fluorophenoxy) pyridin-3-yl] carbonyl} amino) ethyl] benzoic acid; 4-[(1S)-1-({[5-chloro-2-(2,6-difluorophenoxy) pyridin-3-yl] carbonyl} amino) ethyl] benzoic acid; 4-[(1S)-1-({[5-chloro-2-(3,4-difluorophenoxy) pyridin-3-yl] carbonyl} amino) ethyl] benzoic acid; 4-[(1S)-1-({[5-chloro-2-(2,3-difluorophenoxy) pyridin-3-yl] carbonyl} amino) ethyl] benzoic acid; 4-[(1S)-1-({[5-chloro-2-(2,5-difluorophenoxy) pyridin-3-yl] carbonyl} amino) ethyl] benzoic acid; 4-[(1S)-1-({[5-chloro-2-(2-chloro-5-fluorophenoxy) pyridin-3-yl] carbonyl} amino) ethyl] benzoic acid; 4-[(1S)-1-({[5-chloro-2-(3-methylphenoxy) pyridin-3-yl] carbonyl}amino) ethyl] benzoic acid; 4-[(1S)-1-(1 [5-chloro-2-(3,5-difluorophenoxy) pyridin-3-yl] carbonyl} amino) ethyl] benzoic acid; 4-((1S)-1-{[5-chloro-2-(2,3-difluorophenoxy) benzoyl] amino} ethyl) benzoic acid; 4-((1S)-1-{[5-chloro-2-(3,4-difluorophenoxy) benzoyl] amino} ethyl) benzoic acid; 4-[(1S)-1-({[5-chloro-2-(3-chloro-5-fluorophenoxy) pyridin-3-yl] carbonyl} amino) ethyl] benzoic acid; 4-((1S)-1-{[5-chloro-2-(3,5-difluorophenoxy) benzoyl] amino} ethyl) benzoic acid; 4-((1S)-1-{[5-chloro-2-(2,5-difluorophenoxy) benzoyl] amino} ethyl) benzoic acid; 4-[(1S)-1-({[5-chloro-2-(3-chloro-5-methylphenoxy) pyridin-3-yl] carbonyl} amino) ethyl] benzoic acid; 4-((1S)-1-{[5-chloro-2-(3-methylphenoxy) benzoyl] amino} ethyl) benzoic acid; 4-((1S)-1-{[5-chloro-2-(3-chloro-5-fluorophenoxy) benzoyl] amino} ethyl) benzoic acid; 4-((1S)-1-{[5-chloro-2-(2,6-difluorophenoxy) benzoyl] amino} ethyl) benzoic acid; 4-((1S)-1-{[(5-chloro-2-phenoxypyridin-3-yl) carbonyl] amino} ethyl) benzoic acid; 4-[(1S)-1-({[5-chloro-2-(2,3-dichlorophenoxy) pyridin-3-yl] carbonyl} amino) ethyl] benzoic acid; 4-[(1S)-1-({[5-chloro-2-(3,4-dichlorophenoxy) pyridin-3-yl] carbonyl} amino) ethyl] benzoic acid; 4-[(1S)-1-({[5-chloro-2-(3,5-dichlorophenoxy) pyridin-3-yl] carbonyl} amino) ethyl] benzoic acid; and 4-[(1S)-1-({[5-chloro-2-(3-fluoro-4-methylphenoxy) pyridin-3-yl] carbonyl} amino) ethyl] benzoic acid; or a pharmaceutically acceptable salt thereof.

In another preferred aspect, the EP4 receptor ligand (antagonist), which is disclosed in WO 05/105732, is substituted methyl aryl or heteroaryl amide compounds of the following Formula (III)

{Chem. 15}

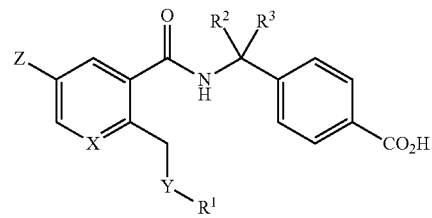

(III)

wherein X represents —CH— or a nitrogen atom;
Y represents —NR$^4$, an oxygen atom or a sulfur atom;
R$^4$ represents a hydrogen atom or an alkyl group having from 1 to 3 carbon atoms;
Z represents a hydrogen atom or a halogen atom;
R$^1$ represents an alkyl group having from 1 to 6 carbon atoms optionally substituted with an alkoxy group having from 1 to 6 carbon atoms or a cycloalkyl group having from 3 to 7 carbon atoms; a cycloalkyl group having from 3 to 7 carbon atoms optionally substituted with an alkyl group having from 1 to 3 carbon atoms; a phenyl group optionally substituted with one or more substituents alpha; or a group Het$^1$ optionally substituted with one or more substituents alpha;
Het$^1$ represents a heterocyclic group having from 4 to 7 ring atoms which contains either from 1 to 4 nitrogen ring heteroatoms or from 0 to 2 nitrogen ring heteroatoms and 1 oxygen or 1 sulfur ring heteroatom;
R$^2$ and R$^3$ independently represent a hydrogen atom or an alkyl group having from 1 to 3 carbon atoms; or R$^2$ and R$^3$ together form an alkylene chain having from 3 to 6 carbon atoms; and
said substituent alpha is selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms, alkanoyl groups having from 2 to 5 carbon atoms, alkenyl groups having from 2 to 4 carbon atoms, alkynyl groups having from 2 to 4 carbon atoms, alkylthio groups having from 1 to 4 carbon atoms, nitro groups, amino groups, mono- or di-alkylamino groups having from 1 to 4 carbon atoms, aminosulfonyl groups, alkoxycarbonyl groups having from 1 to 4 carbon atoms, alkylsufonylamino groups having from 1 to 4 carbon atoms, cycloalkyl groups having from 3 to 7 carbon atoms and a mono- or di-alkylaminocarbonyl groups having from 1 to 6 carbon atoms;
or a pharmaceutically acceptable ester of such compound; or a pharmaceutically acceptable salt thereof.

In the compounds of Formula (III),
Y preferably represents NR$^4$ or an oxygen atom; and R$^4$ represents an alkyl group having from 1 to 3 carbon atoms. More preferably, Y represents NCH$_3$ or an oxygen atom. Most preferably, Y represents an oxygen atom.

In the compounds of Formula (III),
Z preferably represents a halogen atom. More preferably, Z represents a chlorine atom or a fluorine atom.

In the compounds of Formula (III),
R$^1$ preferably represents an alkyl group having from 1 to 6 carbon atoms; a cycloalkyl group having from 3 to 7 carbon atoms, a phenyl group optionally substituted with one or more substituents alpha; or a group Het¹ optionally substituted with one or more substituents alpha;

Het¹ represents a heterocyclic group having from 5 to 6 ring atoms which contains either from 1 to 2 nitrogen ring heteroatoms or from 0 to 2 nitrogen ring heteroatoms and 1 oxygen or 1 sulfur ring heteroatom; said substituents alpha are selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms and alkanoyl groups having from 2 to 5 carbon atoms.

More preferably, R¹ represents an alkyl group having from 1 to 6 carbon atoms, a cycloalkyl group having from 4 to 6 carbon atoms, a phenyl group, a pyridyl group, an oxazolyl group, a pyrazolyl group, a thiazolyl group, a tetrahydrofuranyl group or a tetrahydropyranyl group; said phenyl group, pyridyl group, oxazolyl group, pyrazolyl group, thiazolyl group, tetrahydrofuranyl group and tetrahydropyranyl group referred to in the definitions of R¹ are unsubstituted or are substituted by at least one substituent selected from the group consisting of substituents alpha; said substituents alpha are selected from the group consisting of halogen atoms, alkyl groups having from 1 to 2 carbon atoms and cyano groups. More preferably, R¹ represents a butyl group, a pyridyl group, a phenyl group, an oxazolyl group, a pyrazolyl group or a thiazolyl group; said phenyl group, pyridyl group, oxazolyl group, pyrazolyl group, thiazolyl group referred to in the definitions of R¹ are unsubstituted or are substituted by 1 to 2 substituent selected from the group consisting of substituents alpha; said substituents alpha are selected from the group consisting of halogen atoms and alkyl groups having from 1 to 2 carbon atoms.

Most preferably, R¹ represents a phenyl group, optionally substituted by 1 to 2 groups independently selected from a fluorine atom, a chlorine atom and a methyl group.

In the compounds of Formula (III), preferably, R² and R³ independently represent a hydrogen atom or an alkyl group having from 1 to 3 carbon atoms. More preferably, R² represents a hydrogen atom; and R³ represents a methyl group.

Particularly preferred compounds of the invention include those in which each variable in Formula (III) is selected from the preferred groups for each variable. Even more preferable compounds of the invention include those where each variable in Formula (III) is selected from the more preferred groups for each variable.

A preferred individual compound of Formula (III) is selected from

4-[(1S)-1-({5-Chloro-2-[(4-chlorophenoxy)methyl]benzoyl}amino)ethyl]benzoic acid;
4-[(1S)-1-({5-Chloro-2-[(4-methylphenoxy)methyl]benzoyl}amino)ethyl]benzoic acid;
4-[(1S)-1-({5-Chloro-2-[(3-chlorophenoxy)methyl]benzoyl}amino)ethyl]benzoic acid;
4-[(1S)-1-({5-Chloro-2-[(4-fluorophenoxy)methyl]benzoyl}amino)ethyl]benzoic acid;
4-[(1S)-1-({5-Chloro-2-[(2,3-difluorophenoxy)methyl]benzoyl}amino)ethyl]benzoic acid;
4-[(1S)-1-({5-Chloro-2-[(3,4-difluorophenoxy)methyl]benzoyl}amino)ethyl]benzoic acid;
4-[(1S)-1-({5-Chloro-2-[(2,4-difluorophenoxy)methyl]benzoyl}amino)ethyl]benzoic acid;
4-{(1S)-1-[({5-Chloro-2-[(3-chlorophenoxy)methyl]pyridin-3-yl}carbonyl)amino]ethyl}benzoic acid;
4-[(1S)-1-({5-Chloro-2-[(2-chlorophenoxy)methyl]benzoyl}amino)ethyl]benzoic acid;
4-[(1S)-1-({5-Chloro-2-[(3,5-difluorophenoxy)methyl]benzoyl}amino)ethyl]benzoic acid;
4-{(1S)-1-[({5-Chloro-2-[(4-chlorophenoxy)methyl]pyridin-3-yl}carbonyl)amino]ethyl}benzoic acid;
4-[(1S)-1-({5-Chloro-2-[(3-fluorophenoxy)methyl]benzoyl}amino)ethyl]benzoic acid;
4-[(1S)-1-({5-Chloro-2-[(2,6-difluorophenoxy)methyl]benzoyl}amino)ethyl]benzoic acid;
4-[(1S)-1-({5-Chloro-2-[(2-fluorophenoxy)methyl]benzoyl}amino)ethyl]benzoic acid;
4-[(1S)-1-({5-Chloro-2-[(2,5-difluorophenoxy)methyl]benzoyl}amino)ethyl]benzoic acid; and
4-{(1S)-1-[({2-[(4-Chlorophenoxy)methyl]-5-fluoropyridin-3-yl}carbonyl)amino]ethyl}benzoic acid;

or a pharmaceutically acceptable ester of such compound; or a pharmaceutically acceptable salt thereof.

In another preferred aspect, the EP4 receptor ligand (antagonist), which is disclosed in WO 2004/067524, is a compound of the following Formula (IV) or a pharmaceutically acceptable salt thereof.

{Chem. 16}

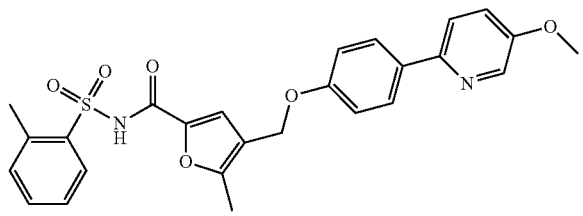

(IV)

A more preferred compound of Formula (IV) is sodium (4-((4-(5-methoxypyridin-2-yl)phenoxy)methyl)-5-methyl-furan-2-carbonyl)(o-tolylsulfonyl)amide.

In another preferred aspect, the EP4 receptor ligand (antagonist), which is disclosed in Marc Blouim et al., J. Med. Chem. (DOI 10.1021/jm901771h) and WO2008/017164, is a compound of the following Formula (Va) or (Vb), or a pharmaceutically acceptable salt thereof:

{Chem. 17}

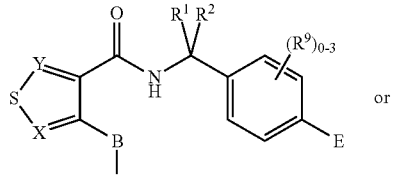

(Va)

or

{Chem. 18}

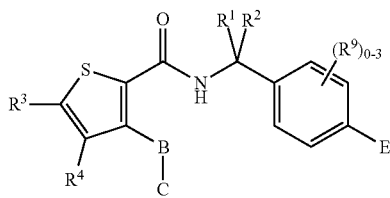 (Vb)

wherein X and Y are independently selected from the group consisting of: N and C(R$^{11}$), wherein each R$^{11}$ is independently selected from the group consisting of: hydrogen, halo and C$_{1-4}$alkyl;

B is selected from the group consisting of: —C(R$^5$)(R$^6$)—, —O—, —S—, —S(O)—, —SO$_2$—, —C(R$^5$)(R$^6$)—C(R$^7$)(R$^8$)—, —O—C(R$^5$)(R$^6$)—, —S—C(R$^5$)(R$^6$)—, —S(O)—C(R$^5$)(R$^6$)— and —SO$_2$—C(R$^5$)(R$^6$)—;

C is selected from the group consisting of aryl and heteroaryl, or a fused analog of aryl or heteroaryl, each optionally substituted with one to three substituents independently selected from R$^{10}$;

E is selected from the group consisting of: —C(O)OH, —C(O)OC$_{1-4}$alkyl, tetrazolyl and

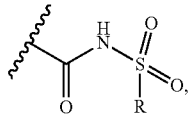 {Chem. 19} wherein R is selected from the group consisting of: C$_{1-4}$alkyl, aryl and heteroaryl, or a fused analog of aryl or heteroaryl, wherein aryl and heteroaryl or the fused analogs thereof are optionally substituted with one to three substituents independently selected from R$^{10}$;

R$^1$ to R$^8$ are independently selected from the group consisting of: H, halo, —O—R$^{12}$, C$_{1-6}$alkyl and C$_{3-6}$cycloalkyl, and one or more pairs of R$^1$ and R$^2$, R$^5$ and R$^6$, and R$^7$ and R$^8$ may be joined together with the carbon atom to which they are attached to form a 3- to 5-membered monocyclic cycloalkyl ring, and R$^5$ and R$^6$ or R$^7$ and R$^8$ may be joined together to form carbonyl;

R$^9$ is independently selected from the group consisting of: halo, hydroxyl and C$_{1-4}$alkyl;

R$^{10}$ is selected from the group consisting of: halo, cyano, C$_{1-4}$alkyl, C$_{1-4}$fluoroalkyl, C$_{1-4}$alkoxy, C$_{1-4}$thioalkoxy and C$_{1-4}$fluoroalkoxy; and each R$^{12}$ is selected from the group consisting of: H, C$_{1-4}$alkyl, C$_{3-6}$cycloalkyl and heterocyclyl.

A preferred individual compound of Formula (Va) or (Vb), is selected from 5-chloro-3-[(3-chlorophenyl)methyl]-N-[1-[4-(2H-tetrazol-5-yl)phenyl]ethyl]-2-thiophenecarboxamide, 2,5-dimethyl-N-[(1S)-1-[4-[[(methylsulfonyl)amino]carbonyl]phenyl]ethyl]-4-[[4-(trifluoromethyl)phenyl]methyl]-3-thiophenecarboxamide, 2,5-dimethyl-N-[(1S)-1-[4-[[(phenylsulfonyl)amino]carbonyl]phenyl]ethyl]-4-[[4-(trifluoromethyl)phenyl]methyl]-3-thiophenecarboxamide, 2,5-dimethyl-N-[1-[4-(2H-tetrazol-5-yl)phenyl]cyclopropyl]-4-[[3-(trifluoromethyl)phenyl]methyl]-3-thiophenecarboxamide, 2,5-dimethyl-N-[1-[4-(2H-tetrazol-5-yl)phenyl]cyclopropyl]-4-[[4-(trifluoromethyl)phenyl]methyl]-3-thiophenecarboxamide, 2-chloro-4-[[[[4-[(3-chlorophenyl)methyl]-2,5-dimethyl-3-thienyl]carbonyl]amino]methyl]-benzoic acid, 4-[(1R)-1-[[[2,5-dichloro-4-[(3-chlorophenyl)methyl]-3-thienyl]carbonyl]amino]ethyl]-benzoic acid, 4-[(1S)-1-[[[2,5-dibromo-4-[(3-chlorophenyl)methyl]-3-thienyl]carbonyl]amino]ethyl]-benzoic acid, 4-[(1S)-1-[[[2,5-dichloro-4-(3-chlorobenzoyl)-3-thienyl]carbonyl]amino]ethyl]-benzoic acid, 4-[(1S)-1-[[[2,5-dichloro-4-[(3-chlorophenyl)[(tetrahydro-2H-pyran-2-yl)oxy]methyl]-3-thienyl]carbonyl]amino]ethyl]-benzoic acid, 4-[(1S)-1-[[[2,5-dichloro-4-[(3-chlorophenyl)hydroxymethyl]-3-thienyl]carbonyl]amino]ethyl]-benzoic acid, 4-[(1S)-1-[[[2,5-dichloro-4-[(3-chlorophenyl)methyl]-3-thienyl]carbonyl]amino]ethyl]-benzoic acid, 4-[(1S)-1-[[[2,5-dichloro-4-[[3-(trifluoromethyl)phenyl]methyl]-3-thienyl]carbonyl]amino]ethyl]-benzoic acid, 4-[(1S)-1-[[[2,5-dimethyl-4-[[3-(trifluoromethyl)phenyl]methyl]-3-thienyl]carbonyl]amino]ethyl]-benzoic acid, 4-[(1S)-1-[[[2,5-dimethyl-4-[[4-(trifluoromethyl)phenyl]methyl]-3-thienyl]carbonyl]amino]ethyl]-benzoic acid, 4-[(1S)-1-[[[2,5-dimethyl-4-[[4-(trifluoromethyl)phenyl]methyl]-3-thienyl]carbonyl]amino]ethyl]-benzoic acid, 4-[(1S)-1-[[[4-[(3-chlorophenyl)methyl]-2,5-dimethyl-3-thienyl]carbonyl]amino]ethyl]-benzoic acid, 4-[(1S)-1-[[[4-[(3-chlorophenyl)methyl]-3-thienyl]carbonyl]amino]ethyl]-benzoic acid, 4-[(1S)-1-[[[4-[(4-chlorophenyl)methyl]-2,5-dimethyl-3-thienyl]carbonyl]amino]ethyl]-benzoic acid, 4-[(1S)-1-[[[5-bromo-4-[(3-chlorophenyl)methyl]-3-thienyl]carbonyl]amino]ethyl]-benzoic acid, 4-[[[[2,5-dichloro-4-[(3-chlorophenyl)methyl]-3-thienyl]carbonyl]amino]methyl]-benzoic acid, 4-[1-[[[2,5-dimethyl-4-[[3-(trifluoromethyl)phenyl]methyl]-3-thienyl]carbonyl]amino]cyclopropyl]-benzoic acid, 4-[1-[[[5-chloro-3-[(3-chlorophenyl)methyl]-2-thienyl]carbonyl]amino]ethyl]-benzoic acid, and 4-{1-[({2,5-dimethyl-4-[4-(trifluoromethyl)benzyl]-3-thienyl}carbonyl)amino]cyclopropyl}benzoic acid.

A preferred compound of this invention is selected from:

3-[2-(4-{2-ethyl-5,7-dimethyl-3H-imidazo[4,5-b]pyridin-3-yl}phenyl)ethyl]-1-[(4-methylbenzene)sulfonyl]urea;

3-[2-(4-{2-ethyl-4,6-dimethyl-1H-imidazo[4,5-c]pyridin-1-yl}phenyl)ethyl]-1-[(4-methylbenzene)sulfonyl]urea;

1-{2-[4-(5-acetyl-2-ethyl-1H-1,3-benzodiazol-1-yl)phenyl]ethyl}-3-[(4-methylbenzene)sulfonyl]urea;

3-{2-[4-(2-ethyl-5-methoxy-1H-1,3-benzodiazol-1-yl)phenyl]ethyl}-1-[(4-methylbenzene)sulfonyl]urea;

2-{4-[6-chloro-2-ethyl-5-(trifluoromethyl)-1H-1,3-benzodiazol-1-yl]phenyl}ethyl N-[(4-methyl benzene)sulfonyl]carbamate;

3-{2-[4-(6-chloro-5-cyano-2-ethyl-1H-1,3-benzodiazol-1-yl)phenyl]ethyl}-1-[(4-methylbenzene)sulfonyl]urea;

2-(4-{2-ethyl-4,6-dimethyl-1H-imidazo[4,5-c]pyridin-1-yl}phenyl)ethyl N-[(4-methylbenzene)sulfonyl]carbamate;

2-(4-{2-tert-butyl-4,6-dimethyl-1H-imidazo[4,5-c]pyridin-1-yl}phenyl)ethyl N-[(4-methyl benzene)sulfonyl]carbamate;

2-[4-(5-carbamoyl-6-chloro-2-ethyl-1H-1,3-benzodiazol-1-yl)phenyl]ethyl N-[(4-methylbenzene)sulfonyl]carbamate;

1-(2-{4-[2-ethyl-5-(1-hydroxyethyl)-1H-1,3-benzodiazol-1-yl]phenyl}ethyl)-3-[(4-methylbenzene)sulfonyl]urea;

1-(2-{4-[6-chloro-2-(2-hydroxypropan-2-yl)-5-(trifluoromethyl)-1H-1,3-benzodiazol-1-yl]phenyl}ethyl)-3-[(4-methylbenzene)sulfonyl]urea;

2-{4-[6-chloro-2-(pyridin-2-yl)-5-(trifluoromethyl)-1H-1,3-benzodiazol-1-yl]phenyl}ethyl N-[(4-methylbenzene)sulfonyl]carbamate;

3-(2-{5-[6-chloro-2-ethyl-5-(trifluoromethyl)-1H-1,3-benzodiazol-1-yl]pyridin-2-yl}ethyl)-1-[(4-methylbenzene)sulfonyl]urea;

2-{4-[6-chloro-2-ethyl-5-(trifluoromethyl)-1H-1,3-benzodiazol-1-yl]phenyl}ethyl N-[(2-chlorobenzene)sulfonyl]carbamate;

3-(2-{4-[5,7-dimethyl-2-(methylamino)-3H-imidazo[4,5-b]pyridin-3-yl]phenyl}ethyl)-1-[(4-methylbenzene)sulfonyl]urea;

4-((1S)-1-{[5-chloro-2-(4-fluorophenoxy)benzoyl]amino}ethyl)benzoic acid;

4-[(1S)-1-({[5-chloro-2-(4-fluorophenoxy)pyridin-3-yl]carbonyl}amino)ethyl]benzoic acid;

4-[(1S)-1({[5-chloro-2-(3-cyanophenoxy)pyridin-3-yl]carbonyl}amino)ethyl]benzoic acid;

4-[(1S)-1-({[5-chloro-2-(3-fluorophenoxy)pyridin-3-yl]carbonyl}amino)ethyl]benzoic acid;

4-[(1S)-1-({[5-chloro-2-(3-chlorophenoxy)pyridin-3-yl]carbonyl}amino)ethyl]benzoic acid;

4-((1S)-1-{[5-chloro-2-(3-fluorophenoxy)benzoyl]amino}ethyl)benzoic acid;

4-((1S)-1-{[5-chloro-2-(3-chlorophenoxy)benzoyl]amino}ethyl)benzoic acid;

4-[(1S)-1-({[5-chloro-2-(2-chloro-4-fluorophenoxy)pyridin-3-yl]carbonyl}amino)ethyl]benzoic acid;

4-[(1S)-1-({[5-chloro-2-(3,4-difluorophenoxy)pyridin-3-yl]carbonyl}amino)ethyl]benzoic acid;

4-[(1S)-1-({[5-chloro-2-(2,3-difluorophenoxy)pyridin-3-yl]carbonyl}amino)ethyl]benzoic acid;

4-((1S)-1-{[5-chloro-2-(2,3-difluorophenoxy)benzoyl]amino}ethyl)benzoic acid;

4-((1S)-1-{[5-chloro-2-(3,4-difluorophenoxy)benzoyl]amino}ethyl)benzoic acid;

4-[(1S)-1-({[5-chloro-2-(3-chloro-5-fluorophenoxy)pyridin-3-yl]carbonyl}amino)ethyl]benzoic acid;

4-[(1S)-1-({5-chloro-2-[(4-chlorophenoxy)methyl]benzoyl}amino)ethyl]benzoic acid;

4-[(1S)-1-({5-chloro-2-[(3-chlorophenoxy)methyl]benzoyl}amino)ethyl]benzoic acid;

4-[(1S)-1-({5-chloro-2-[(4-fluorophenoxy)methyl]benzoyl}amino)ethyl]benzoic acid;

4-[(1S)-1-({5-chloro-2-[(3,4-difluorophenoxy)methyl]benzoyl}amino)ethyl]benzoic acid;

4-[(1S)-1-({5-chloro-2-[(2,4-difluorophenoxy)methyl]benzoyl}amino)ethyl]benzoic acid;

4-{(1S)-1-[({5-chloro-2-[(3-chlorophenoxy)methyl]pyridin-3-yl}carbonyl)amino]ethyl}benzoic acid;

4-[(1S)-1-({5-chloro-2-[(3,5-difluorophenoxy)methyl]benzoyl}amino)ethyl]benzoic acid;

4-[(1S)-1-({5-chloro-2-[(3-fluorophenoxy)methyl]benzoyl}amino)ethyl]benzoic acid;

4-{(1S)-1-[({2-[(4-chlorophenoxy)methyl]-5-fluoropyridin-3-yl}carbonyl)amino]ethyl}benzoic acid;

4-{(1S)-1-({5-chloro-2-[(cyclohexylmethoxy)methyl]benzoyl}amino)ethyl]benzoic acid;

4-((4-(5-methoxypyridin-2-yl)phenoxy)methyl)-5-methyl-N-(o-tolylsulfinyl)furan-2-carboxamide; and 4-{1-[({2,5-dimethyl-4-[4-(trifluoromethyl)benzyl]-3-thienyl}carbonyl)amino]cyclopropyl}benzoic acid, or a pharmaceutically acceptable salt thereof.

Those skilled in the art will fully understand the terms used herein in the description and the appendant claims to describe the present invention. Nonetheless, unless otherwise provided herein, the following terms are as described immediately below.

The term "cartilage disease", as used herein, means diseases associated with destruction, damage or injury of articular cartilage. Examples of such cartilage disease include osteoarthritis, rheumatoid arthritis and arthritis/inflammation associated with cartilage degradation and the like.

By "EP4 receptor antagonist" is meant a chemical substance that reduces or attenuates the biological activity of an EP4 receptor. Such antagonists may include proteins such as anti-EP4 antibodies, nucleic acids, amino acids, peptides carbohydrates, small molecules (organic or inorganic), or any other compound or composition which decreases the activity of an EP4 receptor either by reducing the amount of EP4 receptor present in a cell, or by decreasing the binding or signaling activity of the EP4 receptor.

The term "alkyl", as used herein, means a straight or branched saturated monovalent hydrocarbon radical including, but not limited to, methyl, ethyl, propyl, isopropyl, n-butyl, iso-butyl, sec-butyl, tert-butyl, neopentyl and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butynyl, 2-butynyl and the like.

The term "halo", as used herein, refers to F, Cl, Br or I, preferably F or Cl.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "alkoxy", as used herein, means an O-alkyl group wherein "alkyl" is defined above.

The term "monocyclic aromatic ring", as used herein, means a monocyclic aromatic carbocyclic or heterocyclic ring (and containing 0-4 heteroatoms selected from O, N and S) including, but not limited to, phenyl, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl and the like.

The term "bicyclic aromatic ring", as used herein, means a monocyclic or bicyclic aromatic carbocyclic or heterocyclic ring (and containing 0-4 heteroatoms selected from O, N and S) including, but not limited to, naphthyl, benzofuranyl, isobenzofuranyl, benzothiophenyl, indolyl, isoindolyl, benzoxazolyl, benzothiazolyl, indazolyl, benzimidazolyl, quinolyl, isoquinolyl, cinnolinyl, phthalazinyl, quinazolinyl, quinoxalinyl and the like.

The term "alkylene", as used herein, means a saturated hydrocarbon (straight chain or branched) wherein a hydrogen atom is removed from each of the terminal carbons such as methylene, ethylene, propylene, butylene, pentylene, hexylene and the like.

The term "cycloalkylene", as used herein, means divalent cycloalkyl groups including, but not limited to, cyclopropylene, cyclobutylene, cyclopentylene, cyclohexylene and cycloheptylene and the like.

The term "alkenylene", as used herein, means a straight or branched hydrocarbon chain spacer radical having at least one double bond including, but not limited to, —CH=CH—, —CH=CHCH$_2$—, —CH=CHCH(CH$_3$)—, and the like.

The term "alkynylene", as used herein, means a straight or branched hydrocarbon chain spacer radical having at least one triple bond including, but not limited to,

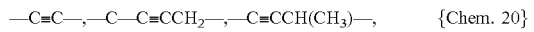  {Chem. 20} and the like.

The term "two adjacent L groups are optionally joined together to form an alkylene chain having 3 or 4 members in which one or two (non-adjacent) carbon atoms are optionally replaced by oxygen atoms", as used herein, means, but not limited to, —O—CH$_2$—O—, —CH$_2$—O—CH$_2$—, —O—CH$_2$CH$_2$—, —CH$_2$CH$_2$—O—, —O—CH$_2$CH$_2$—O—, —CH$_2$CH$_2$CH$_2$—O—, —O—CH$_2$CH$_2$CH$_2$—, —CH$_2$—O—CH$_2$CH$_2$—, —CH$_2$CH$_2$—O—CH$_2$—, and the like.

The term "aryl", as used herein, means aromatic radicals including, but not limited to, phenyl, naphthyl, tetrahydronaphthyl, indanyl, biphenyl and the like.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991).

The term "ester prodrug group" means a protecting group which can be cleaved in vivo by a biological method such as hydrolysis and forms a free acid or salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of groups for an ester of a carboxyl group or a hydroxy group include: (1) aliphatic alkanoyl groups, for example: alkanoyl groups such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups; halogenated alkylcarbonyl groups such as the chloroacetyl, dichloroacetyl, trichloroacetyl, and trifluoroacetyl groups; alkoxyalkanoyl groups such as the methoxyacetyl group; and unsaturated alkanoyl groups such as the acryloyl, propioloyl, methacryloyl, crotonoyl, isocrotonoyl and (E)-2-methyl-2-butenoyl groups; (2) aromatic alkanoyl groups, for example: arylcarbonyl groups such as the benzoyl, alpha-naphthoyl and beta-naphthoyl groups; halogenated arylcarbonyl groups such as the 2-bromobenzoyl and 4-chlorobenzoyl groups; alkylated arylcarbonyl groups such as the 2,4,6-trimethylbenzoyl and 4-toluoyl groups; alkoxylated arylcarbonyl groups such as the 4-anisoyl group; nitrated arylcarbonyl groups such as the 4-nitrobenzoyl and 2-nitrobenzoyl groups; alkoxycarbonylated arylcarbonyl groups such as the 2-(methoxycarbonyl)benzoyl group; and arylated arylcarbonyl groups such as the 4-phenylbenzoyl group; (3) alkoxycarbonyl groups, for example: alkoxycarbonyl groups such as the methoxycarbonyl, ethoxycarbonyl, propoxycarbonyl, butoxycarbonyl, sec-butoxycarbonyl, t-butoxycarbonyl and isobutoxycarbonyl groups; and halogen- or tri(alkyl)silyl-substituted alkoxycarbonyl groups such as the 2,2,2-trichloroethoxycarbonyl and 2-trimethylsilylethoxycarbonyl groups; (4) tetrahydropyranyl or tetrahydrothiopyranyl groups such as: tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups such as: tetrahydrofuran-2-yl and tetrahydrothiofuran-2-yl groups; (5) silyl groups, for example: tri(alkyl)silyl groups such as the trimethylsilyl, triethylsilyl, isopropyldimethylsilyl, t-butyldimethylsilyl, methyldiisopropylsilyl, methyldi-t-butylsilyl and triisopropylsilyl groups; and silyl groups substituted by one or more aryl and alkyl groups such as the diphenylmethylsilyl, diphenylbutylsilyl, diphenylisopropylsilyl and phenyldiisopropylsilyl groups; (6) alkoxymethyl groups, for example: alkoxymethyl groups such as the methoxymethyl, 1,1-dimethyl-1-methoxymethyl, ethoxymethyl, propoxymethyl, isopropoxymethyl, butoxymethyl and t-butoxymethyl groups; alkoxylated alkoxymethyl groups such as the 2-methoxyethoxymethyl group; and halo(alkoxy)methyl groups such as the 2,2,2-trichloroethoxymethyl and bis(2-chloroethoxy)methyl groups; (7) substituted ethyl groups, for example: alkoxylated ethyl groups such as the 1-ethoxyethyl and 1-(isopropoxy)ethyl groups; and halogenated ethyl groups such as the 2,2,2-trichloroethyl group; (8) aralkyl groups, for example: alkyl groups substituted by from 1 to 3 aryl groups such as the benzyl, alpha-naphthylmethyl, beta-naphthylmethyl, diphenylmethyl, triphenylmethyl, alpha-naphthyldiphenylmethyl and 9-anthrylmethyl groups; alkyl groups substituted by from 1 to 3 substituted aryl groups, where one or more of the aryl groups are substituted by one or more alkyl, alkoxy, nitro, halogen or cyano substituents such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups such as the vinyloxycarbonyl; aryloxycarbonyl groups such as phenoxycarbonyl; and aralkyloxycarbonyl groups in which the aryl ring may be substituted by 1 or 2 alkoxy or nitro groups, such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The term "treating", as used herein, refers to reversing, recovering, alleviating, inhibiting, or preventing the onset or the progression of the disorder or condition to which such term applies, or one or more symptoms of such disorder or condition. The term "treatment" as used herein refers to the act of treating, as "treating" is defined immediately above.

It has been known that a compound of formula (I), (II), (III), (IV), (Va) or (Vb) exhibits an excellent EP4 antagonistic activities, and that it shows various effects based on the activities. However, it has never been known that a compound of formula (I), (II), (III), (IV), (Va) or (Vb) normalizes the condition of the cartilage lesion by excellent chondroprotective effect, cartilage destruction suppressing effect and anti-catabolic effect on cartilage.

In this point the present invention is quite different from the above mentioned prior art. Therefore the pharmaceutical composition comprising a compound of formula (I), (II), (III), (IV), (Va) or (Vb) of the present invention is useful for preventing or treating the cartilage disease, that it is especially effective for preventing or treating such disease before sickness reaches bone itself. Therefore the composition can be used not only for treating early stage of a cartilage defect, chronic rheumatoid arthritis and osteoarthritis, but also for preventing these diseases.

Since a compound of formula (I), (II), (Ill), (IV), (Va) or (Vb) has potent cartilage destruction suppressing effect, chondoroprotective effect, anti-catabolic effect on cartilage, inhibition of matrix meralloprotease(MMP)-mediated typeII collagen degradation and MMP-mediated aggrecan degradation, and is more excellent in terms of clinically useful characteristics such as stability, absorption, bioavailability, it can be used for prevention and treatment of a cartilage destruction in a joint in any of various cartilage diseases such as cartilage defect, chronic rheumatoid arthritis involving a cartilage, osteoarthritis involving a cartilage as well as disorders related thereto, in animals (e.g., human, rat, mouse, cat, dog, rabbit, cattle, pig, horse etc.).

Other features and advantages of the invention will be apparent from the following detailed description and from the claims. While the invention is described in connection with specific embodiments, it will be understood that other changes and modifications that may be practiced are also part of this invention and are also within the scope of the appendant claims. This application is intended to cover any equivalents, variations, uses, or adaptations of the invention that follow, in general, the principles of the invention, including departures from the present disclosure that come within known or customary practice within the art. All publications mentioned herein are incorporated by reference in their entireties.

The present invention is directed to the use of an EP4 receptor antagonist in the manufacture of a medicament for the treatment of cartilage diseases.

Therapeutic Methods

Agents identified as EP4 receptor antagonist are administered in a dose effective to treat cartilage diseases. Such therapeutically effective amounts will be determined using routine optimization techniques that are dependent on the particular condition to be treated, the condition of the patient, the route of administration, the formulation, the judgment of the practitioner, and other factors evident to those skilled in the art in light of this disclosure.

For example, i) in case that an EP4 receptor antagonist is Compound A which is orally administered to a human, preferable dose is about 1 mg/day to about 1000 mg/day, preferably, about 10 mg/day to about 800 mg/day, more preferably, about 50 mg/day to about 600 mg/day, and Compound A is preferably administered once a day or twice a day; ii) in case of an EP4 receptor antagonist is Compound A which is orally administered to an animal, preferable dose is about 0.1 mg/kg/day to about 10 mg/kg/day, preferably, about 0.5 mg/kg/day to about 6 mg/kg/day; more preferably, about 1 mg/kg/day to about 4 mg/kg/day and Compound A is preferably administered once a day or twice a day; and iii) in case that an EP4 receptor antagonist is Compound A which is intraarticularly administered to a human or an animal, the preferable dose is about 0.005 µg to about 50 mg, preferably, about 0.01 µg to about 10 mg, more preferably, about 0.1 µg to about 3 mg and Compound A is preferably administered in the range of about once a week to about once a month. If Compound A is administered to a human or an animal within any of the above preferable doses, the effect of Compound A may be enough exhibited, and side effects caused by Compound A may be limited. Further, the above preferable doses of Compound A of the present invention are remarkably less than the doses of other EP4 receptor antagonists.

An agent that inhibits EP4 activity can be incorporated into a therapeutic composition. Such EP4 receptor antagonists can include small molecules, nucleic acids, e.g., EP4 antisense nucleic acids, amino acids, peptides, carbohydrates, and anti-EP4 antibodies. Preferably, such agents are combined with a pharmaceutically acceptable delivery vehicle or carrier. Examples of EP4 antibodies include, for example, polyclonal, monoclonal, humanized, anti-idiotypic, chimeric or single chain antibodies, Fab, F(ab')$_2$, and Fab expression library fragments, scFV molecules, and epitope-binding fragments thereof. An antisense oligonucleotide directed to the EP4 gene or mRNA to inhibit its expression is made according to standard techniques (see, e.g., Agrawal et al., *Methods in Molecular Biology: Protocols for Oligonucleotides and Analogs*, Vol. 20 (1993)).

As used herein, a pharmaceutically acceptable delivery vehicle includes solvents, dispersion media, coatings, antibacterial and antifungal agents, and isotonic and absorption delaying agents that are compatible with pharmaceutical administration. The vehicle may also include other active or inert components, and/or may be targeted to joint tissue by virtue of its composition.

A therapeutic composition is formulated to be compatible with its intended route of administration. Non-limiting examples of routes of administration include parenteral, e.g., intravenous, intradermal, subcutaneous, oral (e.g., by ingestion or inhalation), transdermal (topical), transmucosal, and rectal administration. Solutions or suspensions can be made as described in *Remington's Pharmaceutical Sciences*, (18$^{th}$ ed., Gennaro, ed., Mack Publishing Co., Easton, Pa., (1990)).

Therapeutic efficacy of such EP4 antagonists can be determined in light of this disclosure by standard therapeutic procedures in cell cultures or experimental animals, e.g., for determining the ED$_{50}$ (the dose therapeutically effective in 50% of the population).

The data obtained from the cell culture assays and animal studies can be used in formulating a range of dosage for use in humans. The dosage may vary depending upon the formulation and the route of administration. For any EP4 antagonist used in the method of the invention, the therapeutically effective dose can be estimated initially from cell culture assays. A dose may be formulated in animal models to achieve a circulating plasma concentration range that includes the IC$_{50}$ as determined in cell culture. Such information can be used to more accurately determine useful doses in humans. Levels in plasma may be measured, for example, by high performance liquid chromatography.

The compound with EP4 antagonistic activity, or a pharmaceutically acceptable salt thereof can be used in combination with one or more additional compounds known to be useful in the treatment or prevention of cartilage disease or the symptoms thereof. Such example includes, but not limited to, NSAIDs, COX-2 inhibitors, steroids, matrix metalloproteinase inhibitors and hyaluronic acid.

The skilled artisan will appreciate that certain factors may influence the dosage and timing required to effectively treat a mammal including, but not limited to, the severity of the disease or disorder, previous treatments, the general health and/or age of the mammal, and other diseases present. Moreover, treatment of a mammal with a therapeutically effective amount of an EP4 antagonist can include a single treatment or, preferably, can include a series of treatments.

EXAMPLES

Compounds List:
- 3-[2-(4-{2-ethyl-5,7-dimethyl-3H-imidazo[4,5-b]pyridin-3-yl}phenyl)ethyl]-1-[(4-methylbenzene)sulfonyl]urea;
- 3-[2-(4-{2-ethyl-4,6-dimethyl-1H-imidazo[4,5-c]pyridin-1-yl}phenyl)ethyl]-1-[(4-methylbenzene)sulfonyl]urea (Compound A);
- 1-{2-[4-(5-acetyl-2-ethyl-1H-1,3-benzodiazol-1-yl)phenyl]ethyl}-3-[(4-methylbenzene)sulfonyl]urea;
- 3-{2-[4-(2-ethyl-5-methoxy-1H-1,3-benzodiazol-1-yl)phenyl]ethyl}-1-[(4-methylbenzene)sulfonyl]urea;
- 2-{4-[6-chloro-2-ethyl-5-(trifluoromethyl)-1H-1,3-benzodiazol-1-yl]phenyl}ethyl N-[(4-methylbenzene)sulfonyl]carbamate;
- 3-{2-[4-(6-chloro-5-cyano-2-ethyl-1H-1,3-benzodiazol-1-yl)phenyl]ethyl}-1-[(4-methylbenzene)sulfonyl]urea;
- 2-(4-{2-ethyl-4,6-dimethyl-1H-imidazo[4,5-c]pyridin-1-yl}phenyl)ethyl N-[(4-methylbenzene)sulfonyl]carbamate;
- 2-(4-{2-tert-butyl-4,6-dimethyl-1H-imidazo[4,5-c]pyridin-1-yl}phenyl)ethyl N-[(4-methylbenzene)sulfonyl]carbamate;
- 2-[4-(5-carbamoyl-6-chloro-2-ethyl-1H-1,3-benzodiazol-1-yl)phenyl]ethyl N-[(4-methyl benzene)sulfonyl]carbamate;
- 1-(2-{4-[2-ethyl-5-(1-hydroxyethyl)-1H-1,3-benzodiazol-1-yl]phenyl}ethyl)-3-[(4-methylbenzene)sulfonyl]urea;
- 1-(2-{4-[6-chloro-2-(2-hydroxypropan-2-yl)-5-(trifluoromethyl)-1H-1,3-benzodiazol-1-yl]phenyl}ethyl)-3-[(4-methylbenzene)sulfonyl]urea;
- 2-{4-[6-chloro-2-(pyridin-2-yl)-5-(trifluoromethyl)-1H-1,3-benzodiazol-1-yl]phenyl}ethyl N-[(4-methylbenzene)sulfonyl]carbamate;
- 3-(2-{5-[6-chloro-2-ethyl-5-(trifluoromethyl)-1H-1,3-benzodiazol-1-yl]pyridin-2-yl}ethyl)-1-[(4-methylbenzene)sulfonyl]urea;
- 2-{4-[6-chloro-2-ethyl-5-(trifluoromethyl)-1H-1,3-benzodiazol-1-yl]phenyl}ethyl N-[(2-chlorobenzene)sulfonyl]carbamate;
- 3-(2-{4-[5,7-dimethyl-2-(methylamino)-3H-imidazo[4,5-b]pyridin-3-yl]phenyl}ethyl)-1-[(4-methylbenzene)sulfonyl]urea;
- 4-((1S)-1-{[5-chloro-2-(4-fluorophenoxy)benzoyl]amino}ethyl)benzoic acid;
- 4-[(1S)-1-({[5-chloro-2-(4-fluorophenoxy)pyridin-3-yl]carbonyl}amino)ethyl]benzoic acid;
- 4-[(1S)-1({[5-chloro-2-(3-cyanophenoxy)pyridin-3-yl]carbonyl}amino)ethyl]benzoic acid;
- 4-[(1S)-1-({[5-chloro-2-(3-fluorophenoxy)pyridin-3-yl]carbonyl}amino)ethyl]benzoic acid (Compound B);
- 4-[(1S)-1-({[5-chloro-2-(3-chlorophenoxy)pyridin-3-yl]carbonyl}amino)ethyl]benzoic acid;
- 4-((1S)-1-{[5-chloro-2-(3-fluorophenoxy)benzoyl]amino}ethyl)benzoic acid;
- 4-((1S)-1-{[5-chloro-2-(3-chlorophenoxy)benzoyl]amino}ethyl)benzoic acid;
- 4-[(1S)-1-({[5-chloro-2-(2-chloro-4-fluorophenoxy)pyridin-3-yl]carbonyl}amino)ethyl]benzoic acid;
- 4-[(1S)-1-({[5-chloro-2-(3,4-difluorophenoxy)pyridin-3-yl]carbonyl}amino)ethyl]benzoic acid;
- 4-[(1S)-1-({[5-chloro-2-(2,3-difluorophenoxy)pyridin-3-yl]carbonyl}amino)ethyl]benzoic acid;
- 4-((1S)-1-{[5-chloro-2-(2,3-difluorophenoxy)benzoyl]amino}ethyl)benzoic acid;
- 4-((1S)-1-{[5-chloro-2-(3,4-difluorophenoxy)benzoyl]amino}ethyl)benzoic acid;
- 4-[(1S)-1-({[5-chloro-2-(3-chloro-5-fluorophenoxy)pyridin-3-yl]carbonyl}amino)ethyl]benzoic acid;
- 4-[(1S)-1-({5-chloro-2-[(4-chlorophenoxy)methyl]benzoyl}amino)ethyl]benzoic acid;
- 4-[(1S)-1-({5-chloro-2-[(3-chlorophenoxy)methyl]benzoyl}amino)ethyl]benzoic acid;
- 4-[(1S)-1-({5-chloro-2-[(4-fluorophenoxy)methyl]benzoyl}amino)ethyl]benzoic acid;
- 4-[(1S)-1-({5-chloro-2-[(3,4-difluorophenoxy)methyl]benzoyl}amino)ethyl]benzoic acid;
- 4-[(1S)-1-({5-chloro-2-[(2,4-difluorophenoxy)methyl]benzoyl}amino)ethyl]benzoic acid;
- 4-{(1S)-1-[({5-chloro-2-[(3-chlorophenoxy)methyl]pyridin-3-yl}carbonyl)amino]ethyl}benzoic acid (Compound C);
- 4-[(1S)-1-({5-chloro-2-[(3,5-difluorophenoxy)methyl]benzoyl}amino)ethyl]benzoic acid;
- 4-[(1S)-1-({5-chloro-2-[(3-fluorophenoxy)methyl]benzoyl}amino)ethyl]benzoic acid;
- 4-{(1S)-1-[({2-[(4-chlorophenoxy)methyl]-5-fluoropyridin-3-yl}carbonyl)amino]ethyl}benzoic acid;
- 4-{(1S)-1-({5-chloro-2-[(cyclohexylmethoxy)methyl]benzoyl}amino)ethyl}benzoic acid;
- 4-((4-(5-methoxypyridin-2-yl)phenoxy)methyl)-5-methyl-N-(o-tolylsulfonyl)furan-2-carboxamide (Compound D),
- 4-{1-[({2,5-dimethyl-4-[4-(trifluoromethyl)benzyl]-3-thienyl}carbonyl)amino]cyclopropyl}benzoic acid (Compound E),
- 5-chloro-3-[(3-chlorophenyl)methyl]-N-[1-[4-(2H-tetrazol-5-yl)phenyl]ethyl]-2-thiophenecarboxamide,
- 2,5-dimethyl-N-[(1S)-1-[4-[[(methylsulfonyl)amino]carbonyl]phenyl]ethyl]-4-[[4-(trifluoromethyl)phenyl]methyl]-3-thiophenecarboxamide,
- 2,5-dimethyl-N-[(1S)-1-[4-[[(phenylsulfonyl)amino]carbonyl]phenyl]ethyl]-4-[[4-(trifluoromethyl)phenyl]methyl]-3-thiophenecarboxamide,
- 2,5-dimethyl-N-[1-[4-(2H-tetrazol-5-yl)phenyl]cyclopropyl]-4-[[3-(trifluoromethyl)phenyl]methyl]-3-thiophenecarboxamide,
- 2,5-dimethyl-N-[1-[4-(2H-tetrazol-5-yl)phenyl]cyclopropyl]-4-[[4-(trifluoromethyl)phenyl]methyl]-3-thiophenecarboxamide,
- 2-chloro-4-[[[4-[(3-chlorophenyl)methyl]-2,5-dimethyl-3-thienyl]carbonyl]amino]methyl]-benzoic acid,
- 4-[(1R)-1-[[[2,5-dichloro-4-[(3-chlorophenyl)methyl]-3-thienyl]carbonyl]amino]ethyl]-benzoic acid,
- 4-[(1S)-1-[[[2,5-dibromo-4-[(3-chlorophenyl)methyl]-3-thienyl]carbonyl]amino]ethyl]-benzoic acid,
- 4-[(1S)-1-[[[2,5-dichloro-4-(3-chlorobenzoyl)-3-thienyl]carbonyl]amino]ethyl]-benzoic acid,
- 4-[(1S)-1-[[[2,5-dichloro-4-[(3-chlorophenyl)[(tetrahydro-2H-pyran-2-yl)oxy]methyl]-3-thienyl]carbonyl]amino]ethyl]-benzoic acid,
- 4-[(1S)-1-[[[2,5-dichloro-4-[(3-chlorophenyl)hydroxymethyl]-3-thienyl]carbonyl]amino]ethyl]-benzoic acid,
- 4-[(1S)-1-[[[2,5-dichloro-4-[(3-chlorophenyl)methyl]-3-thienyl]carbonyl]amino]ethyl]-benzoic acid,
- 4-[(1S)-1-[[[2,5-dichloro-4-[[3-(trifluoromethyl)phenyl]methyl]-3-thienyl]carbonyl]amino]ethyl]-benzoic acid,
- 4-[(1S)-1-[[[2,5-dimethyl-4-[[3-(trifluoromethyl)phenyl]methyl]-3-thienyl]carbonyl]amino]ethyl]-benzoic acid,
- 4-[(1S)-1-[[[2,5-dimethyl-4-[[4-(trifluoromethyl)phenyl]methyl]-3-thienyl]carbonyl]amino]ethyl]-benzoic acid,
- 4-[(1S)-1-[[[2,5-dimethyl-4-[[4-(trifluoromethyl)phenyl]methyl]-3-thienyl]carbonyl]amino]ethyl]-benzoic acid,
- 4-[(1S)-1-[[[4-[(3-chlorophenyl)methyl]-2,5-dimethyl-3-thienyl]carbonyl]amino]ethyl]-benzoic acid, 4-[(1S)-1-[[[4-[(3-chlorophenyl)methyl]-3-thienyl]carbonyl]amino]ethyl]-benzoic acid,
4-[(1S)-1-[[[4-[(4-chlorophenyl)methyl]-2,5-dimethyl-3-thienyl]carbonyl]amino]ethyl]-benzoic acid,
4-[(1S)-1-[[[5-bromo-4-[(3-chlorophenyl)methyl]-3-thienyl]carbonyl]amino]ethyl]-benzoic acid,
4-[[[[2,5-dichloro-4-[(3-chlorophenyl)methyl]-3-thienyl]carbonyl]amino]methyl]-benzoic acid,
4-[1-[[[2,5-dimethyl-4-[[3-(trifluoromethyl)phenyl]methyl]-3-thienyl]carbonyl]amino]cyclopropyl]-benzoic acid,
4-[1-[[[5-chloro-3-[(3-chlorophenyl)methyl]-2-thienyl]carbonyl]amino]ethyl]-benzoic acid, and
Compound A, Compound B, Compound C, Compound D or Compound E is a representative compound in Formula (I), Formula (II), Formula (III), Formula (IV) and Formula (Va, Vb), respectively.

A compound which has EP4 receptor antagonistic activity can be confirmed by known method (For example, Eur J Pharmacol. 1997: 340: 227-241). The in vitro assays for assessing EP4 receptor antagonistic activity are typically membrane binding assay and cell-based functional assay. The binding activity of compounds for EP4 receptor was determined with using membrane prepared from HEK293 cells expressing EP4 receptor and radiolabeled ligands PGE2. The antagonistic activity of compounds on the EP4 receptor was determined by using HEK293 cells expressing EP4 receptor and PGE2. The inhibition of the PGE2-evoked cAMP level by compounds was analyzed.

Example 1: Ex Vivo Bovine Cartilage Explant Model

The method of this assay is descrived in the following literature (Rheumatol Int. 2013 February; 33(2):401-11).
Full-depth cartilage explants were harvested from the knee of either back legs of a cow less than 24 month old. All the FDC explants are divided into different treatment group according to the explants weight and metabolic activity (viability) measured by Alamar Blue. Compounds were freshly added to the explants at each media change. The explants were cultured in serum-free conditions. Supernatants retrieved from the culture were analyzed by biomarkers (P2NP, C2M, AGNx1, AGNx2) at day 7, 14 and 21.
These results are shown in FIG. 1 and FIG. 2.
From results of FIG. 1, Compound A and Compound B shows dose-dependent inhibition of cartilage destruction in ex vivo bovine cartilage explant model
The similar inhibition of cartilage destruction in ex vivo bovine cartilage explant model is shown in Compound C (4-{(1S)-1-[({5-chloro-2-[(3-chlorophenoxy)methyl]pyridin-3-yl}carbonyl)amino]ethyl}benzoic acid), Compound D (4-((4-(5-methoxypyridin-2-yl)phenoxy)methyl)-5-methyl-N-(o-tolylsulfonyl)furan-2-carboxamide) and Compound E (4-{1-[({2,5-dimethyl-4-[4-(trifluoromethyl)benzyl]-3-thienyl}carbonyl)amino]cyclopropyl}benzoic acid).
The compounds describe in the compounds list are similarly conducted in this cartilage destruction assay. The dose-dependent inhibition of cartilage destruction in ex vivo bovine cartilage explant model is observed in all cases. ####p<0.0001 versus disease control by ANOVA test.

Example 2: Rat Mono-Iodoacetate and/or Meniscal Transection Model

The compounds described in the compounds list are conducted in the rat mono-iodoacetate and/or meniscal transection induced osteoarthritis model. These compounds exhibit potent inhibitory activities on cartilage destruction and serum biochemical markers associated with cartilage degradation and tissue inflammation in the rat mono-iodoacetate and/or meniscal transection model.

The study was performed in female Sprague-Dawley rats, age 6 months at MNX surgery.
7 days after MNX surgery monoiodoacetate 2 mg/0.2 ml was injected intraarticularly in the right knee joint. The test compounds or vehicle is injected to the animals after the MNX. In the MNX or sham group, the test compounds or vehicle was administered until termination.
Weekly fasting blood sampling are taken for the analysis of biomarker (P2NP, C2M, AGNx1, AGNx2). Knee joints is isolated at termination. Cartilage damage is scored by experienced histo-pathologist according to Colombo score.
The compounds described in the compounds list are similarly conducted in rat mono-iodoacetate and/or meniscal transection model. The potent activities are observed in all cases.

Example 3: Rat Meniscal Transection and/or Ovariectomised Model

The compounds describe in the compounds list are conducted in the rat meniscal (MNX) transection and/or ovariectomised (OVA) induced osteoarthritis model. These compounds exhibit excellent inhibitory activities on cartilage destruction and serum biochemical markers associated with cartilage degradation and tissue inflammation in the rat meniscal transection and/or ovariectomised model.

The study is performed in female Sprague-Dawley rats with MNX and OVX surgery.
The test compounds or vehicle is injected to the animals after the surgery. In the MNX/OVX or sham group, the test compounds or vehicle was administered until termination.
Weekly fasting blood sampling are taken for the analysis of biomarker (P2NP, C2M, AGNx1, AGNx2). Knee joints is isolated at termination. Cartilage damage is scored by experienced histo-pathologist according to Colombo score.
The compounds describe in the compounds list are similarly conducted in rat mono-iodoacetate and/or meniscal transection model. The potent activities are observed in all cases.

INDUSTRIAL APPLICABILITY

According to the present invention, a compound of formula (I), (II), (III), (IV), (Va) or (Vb), or a pharmaceutically acceptable salt thereof is useful for the treatment and/or prevention of cartilage disease.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:
1. A method for inhibiting cartilage destruction, which comprises orally administering to an animal or a human in need thereof a therapeutically effective amount of 3-[2-(4-{2-ethyl-4,6-dimethyl-1H-imidazo[4,5-c]pyridin-1- yl}phenyl)ethyl]-1-[(4-methylbenzene)sulfonyl]urea or a pharmaceutically acceptable salt thereof,
  wherein the therapeutically effective amount of the 3-[2-(4-{2-ethyl-4,6-dimethyl-1H-imidazo[4,5-c]pyridin-1-yl}phenyl)ethyl]-1-[(4-methylbenzene)sulfonyl]urea or pharmaceutically acceptable salt thereof which is orally administered to the human is about 1 mg/day to about 1000 mg/day, and
  wherein the therapeutically effective amount of the 3-[2-(4-{2-ethyl-4,6-dimethyl-1H-imidazo[4,5-c]pyridin-1-yl}phenyl)ethyl]-1-[(4-methylbenzene)sulfonyl]urea or pharmaceutically acceptable salt thereof which is orally administered to the animal is about 0.1 mg/kg/day to about 10 mg/kg/day.

2. The method according to claim 1, wherein the therapeutically effective amount of the 3-[2-(4-{2-ethyl-4,6-dimethyl-1H-imidazo[4,5-c]pyridin-1-yl}phenyl)ethyl]-1-[(4-methylbenzene)sulfonyl]urea or pharmaceutically acceptable salt thereof which is orally administered to the human or the animal is administered once a day or twice a day.

3. The method according to claim 1, which further comprises administering a therapeutically effective amount of one or more additional compounds known to be useful in the treatment or prevention of a cartilage disease or a symptom thereof.

4. The method according to claim 3, wherein the one or more additional compounds known to be useful in the treatment or prevention of the cartilage disease or the symptom thereof is selected from the group consisting of an NSAID, a COX-2 inhibitor, a steroid, a matrix metalloproteinase inhibitor and hyaluronic acid.

5. A method for inhibiting cartilage destruction, which comprises intraarticularly administering to an animal or a human in need thereof a therapeutically effective amount of 3-[2-(4-{2-ethyl-4,6-dimethyl-1H-imidazo[4,5-c]pyridin-1-yl}phenyl)ethyl]-1-[(4-methylbenzene)sulfonyl]urea or a pharmaceutically acceptable salt thereof, wherein the therapeutically effective amount of the 3-[2-(4-{2-ethyl-4,6-dimethyl-1H-imidazo[4,5-c]pyridin-1-yl}phenyl)ethyl]-1-[(4-methylbenzene)sulfonyl]urea or pharmaceutically acceptable salt thereof which is intraarticularly administered to the human or the animal is about 0.005 μg to about 50 mg.

6. The method according to claim 5, wherein the therapeutically effective amount of the 3-[2-(4-{2-ethyl-4,6-dimethyl-1H-imidazo[4,5-c]pyridin-1-yl}phenyl)ethyl]-1-[(4-methylbenzene)sulfonyl]urea or pharmaceutically acceptable salt thereof which is intraarticularly administered to the human or animal is administered in the range of about once a week to about once a month.

7. The method according to claim 5, which further comprises administering a therapeutically effective amount of one or more additional compounds known to be useful in the treatment or prevention of a cartilage disease or a symptom thereof.

8. The method according to claim 7, wherein the one or more additional compounds known to be useful in the treatment or prevention of the cartilage disease or the symptom thereof is selected from the group consisting of an NSAID, a COX-2 inhibitor, a steroid, a matrix metalloproteinase inhibitor and hyaluronic acid.

* * * * *